United States Patent
Inagaki et al.

(10) Patent No.: US 8,076,307 B2
(45) Date of Patent: Dec. 13, 2011

(54) FORMATION/ELONGATION OF AXON BY INHIBITING THE EXPRESSION OR FUNCTION OF SINGAR AND APPLICATION TO NERVE REGENERATION

(75) Inventors: Naoyuki Inagaki, Ikoma (JP); Tatsuya Mori, Wako (JP); Osamu Ohara, Kisarazu (JP); Takahiro Nagase, Kisarazu (JP)

(73) Assignees: National University Corporation Nara Institute of Science and Technology, Ikoma-shi (JP); Kazusa DNA Research Institute, Kisarazu-shi (JP)

( * ) Notice: Subject to any disclaimer, the term of this patent is extended or adjusted under 35 U.S.C. 154(b) by 606 days.

(21) Appl. No.: 12/084,242

(22) PCT Filed: Oct. 26, 2006

(86) PCT No.: PCT/JP2006/321364
§ 371 (c)(1),
(2), (4) Date: Jun. 13, 2008

(87) PCT Pub. No.: WO2007/049690
PCT Pub. Date: May 3, 2007

(65) Prior Publication Data
US 2010/0267072 A1    Oct. 21, 2010

(30) Foreign Application Priority Data

Oct. 27, 2005 (JP) .................................. 2005-313406

(51) Int. Cl.
*C12N 15/11* (2006.01)
*C12N 15/00* (2006.01)
*C07H 21/04* (2006.01)
(52) U.S. Cl. ...................... 514/44 A; 435/455; 536/24.5
(58) Field of Classification Search ........................ None
See application file for complete search history.

(56) References Cited

U.S. PATENT DOCUMENTS

| 7,056,704 B2 * | 6/2006 | Tuschl et al. | 435/91.1 |
| 2003/0003538 A1 * | 1/2003 | Dietrich et al. | 435/69.1 |
| 2005/0042646 A1 * | 2/2005 | Davidson et al. | 435/6 |

OTHER PUBLICATIONS

Ebert et al., "Mus musculus full open reading frame cDNA clone RZPDo836H0653D for gene D5Bwg0860e, DNA segment," Chr 5, Brigham & Women's Genetics 0860 expressed; complete cds, incl stopcodon. Database DDBJ/EMBL/GenBank [online], Accession No. CT010404, <http://www.ncbi.nlm.nih.gov/21-JUL-2005 uploaded.
Strausberg et al., "*Homo sapiens* rap2 interacting protein x, mRNA (cDNA clone MGC: 48314 Image: 5265230), complete cds," Database DDBJ/EMBL/GenBank [online], Accession No. BC051716, http://www.ncbi.nlm.nih.gov/entrez/viewer, fcgi?30704842:NCBI:10740578 Jul. 30, 2005 uploaded.
Strausberg et al., "*Rattus norvegicus* rap2 interacting protein x, mRNA (cDNA clone MGC: 109279 Image: 7312240), complete cds," Database DDBJ/EMBL/ GenBank [online], Accession No. BC089952, http://www.ncbi.nlm.nih.gov/ entrez/viewer, fcgi?58477175:NCBI:10684071>Jul. 25, 2005 uploaded.
MacDonald et al., "Nesca: A novel adapter, translocates to the nuclear envelope and regulates neurotrophin-induced neurite outgrowth," *J. Cell Biol.* vol. 164, No. 6, Mar. 15, 2004, pp. 851-862.
Ogura et al., "The UNC-14 protein required for axonal elongation and guidance in *Caenorhabditis elegans* interacts with the serine/threonine kinase UNC-51," *Genes & Development*, vol. 11, No. 14, pp. 1801-1811, 1997.
Inagaki et al., "Long gel two-dimensional electrophoresis* Improving recovery of cellular proteome," *Current Proteomics*, vol. 1, No. 1, pp. 35-39, 2004.
Oguri et al., "Proteome analysis of rat hippocampal neurons by multiple large gel two-dimensional electrophoresis," *Proteomics*, vol. 2, No. 6, pp. 666-672, Jun. 2002.
Strausberg et al., "Mus musculus DNA segment," Chr 5, Brigham & Women's Genetics 0860 expressed, Mrna (Cdna CLONE mgc: 68268 Image:6469137), complete cds, Database DDBJ/EMBL/ GenBank [online], Accession No. BC058259, http://www.ncbi.nlm.nih.gov/ entrez/viewer, fcgi?34849577:OLD:1044367>Nov. 4, 2003 uploaded.
Dotti et al., "The establishment of polarity by hippocampal neurons in culture," *The Journal of Neuroscience*, Apr. 1988, vol. 8, No. 4, pp. 1454-1468.

* cited by examiner

*Primary Examiner* — Richard Schnizer
(74) *Attorney, Agent, or Firm* — Fitch, Even, Tabin & Flannery

(57) ABSTRACT

Singar is identified as a novel molecule, whose expression is varied before and after the polarization of a nerve cell, and occurs in the tip of an elongating axon, called a growth cone, which is important for the formation or elongation of an axon. Singar is expressed specifically in the brain and the amount of Singar expression is largely increased in an individual during periods where the formation of axons is increased. It is observed that Singar is highly enriched in the growth cone at the tip of an axon. When the expression of Singar is inhibited in nerve cells in culture, the formation of multiple axons is induced. Thus, the inhibition of Singar can induce axon formation. Therefore, by inhibiting the expression or activity of Singar, it becomes possible to induce or promote the formation or elongation of an axon in a nerve cell.

4 Claims, 5 Drawing Sheets

Fig.2
(a)
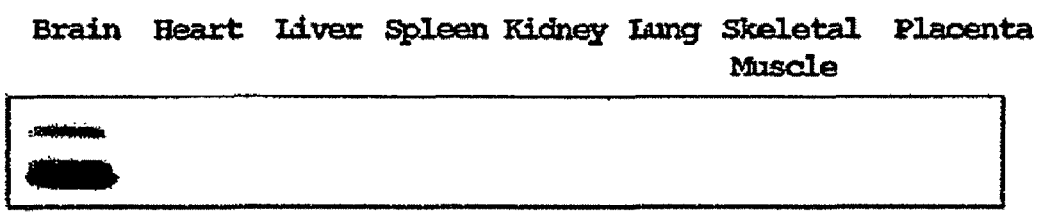
(b)
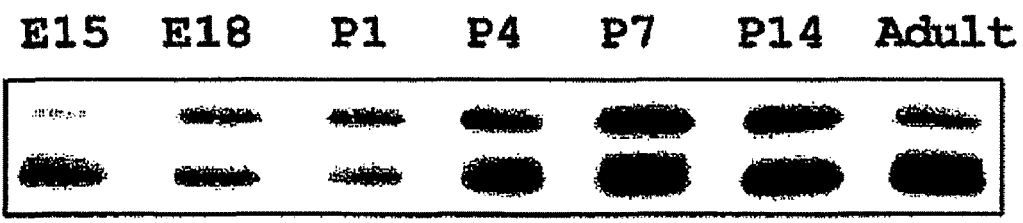
(c)
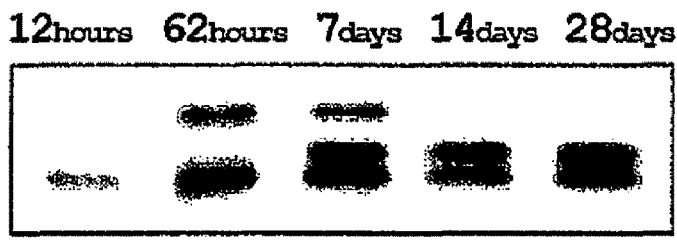

Fig.3
(a)
(b)
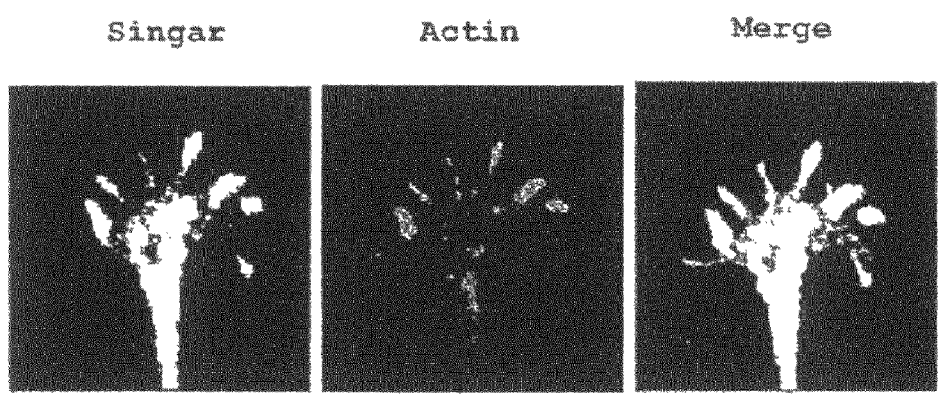
Fig.4
siRNA Target Seq. ① : 395-CUCUAGAGCUGGUAGAAAA
siRNA Target Seq. ② : 846-GGCAAAAGUAGAUGCGUUA
scRNA Seq. : AGCGAAGGUUGACGCUCUU

US 8,076,307 B2

FORMATION/ELONGATION OF AXON BY INHIBITING THE EXPRESSION OR FUNCTION OF SINGAR AND APPLICATION TO NERVE REGENERATION

TECHNICAL FIELD

The present invention relates to a method for suppressing the expression or function of Singar, which is a protein specifically expressed in the brain, thereby inducing or promoting axon formation or elongation in a neuron. The present invention in particular contributes to the development of novel nerve regeneration technology, for example, and can be employed in the research and establishment of axon regeneration medical technologies, such as effective remedies for damage to the central and peripheral nerves caused by stroke or spinal cord injury, and could be used for establishing medical technology for axonal regeneration and during the development thereof.

BACKGROUND ART

Neurons are cells that possess polarity by themselves, that is, they process directionality. Namely, neurons have multiple dendrites and a single axon, receive information from other neurons at their dendrites, and integrate the inputs within their cell body to convert them into an action potential that transmits over the axon from the cell body to the synaptic terminal. Neurotransmitters are then released from the synaptic terminus to transmit information to a target cell. This phenomenon is the basis for higher-order life activities such as memory, learning and exercise in higher organisms. Most of polarity formation in a neuron and the molecular mechanisms of maintenance, however, remain unknown (for research regarding polarity formation, see for example Dotti, C. G., Sullivan, C. A., Banker, G. A. (1988) The Establishment of Polarity by Hippocampal Neurons in Culture. J. Neurosci. 8, 1454-1468).

Deciphering the molecular mechanisms of polarity formation in a neuron would elucidate the molecular mechanisms of axon formation and elongation during the developmental stage, and also those of the formation of neural networks. The formation of polarity is one aspect of axon formation in a neuron. When the molecules involved in the polarity formation is identified, the molecules could be employed to form or elongate nerve axons. There is also a possibility that those same molecules could be utilized in the development of a novel nerve regeneration technology, such as could be used in the development of medical therapies for the regeneration of severed or degenerated nerve axons.

The development of such therapies is of great importance. For example, there are no effective drug therapies for axonal regeneration of the central and peripheral nerve damage caused by stroke or trauma, and currently the primary medical approach for such damage is rehabilitation to recover nerve function. In particular, once impaired, the axons of central nerves cannot be regenerated, often confining the patient to a wheel-chair for life. This makes the disorder a high burden on the patients, their families, and society.

DISCLOSURE OF THE INVENTION

Problems to be Solved by the Invention

The primary object of the present invention is to develop and provide a novel method for inducing and/or promoting axon formation and/or elongation in a neuron. The method comprises, by way of proteome analysis such as two-dimensional electrophoresis, mass analysis or the like, identifying the molecules whose expression changes before and after polarity formation in the neurons, and are localized in the growth cones at the tip of the axons that are important for axon formation and/or elongation; and analyzing the function of such a molecule. The secondary object of the present invention is to provide an axon formation (or elongation) inducer usable in said method and in nerve regeneration therapy for central and peripheral nerve damage. Further, the tertiary object of the present invention is to provide a screening method for therapeutic neuronal regeneration agents targeting said molecules or using them as probes.

Means for Solving the Problems

The present inventors screened proteins in cultured rat hippocampal neurons using proprietary highly sensitive two-dimensional electrophoresis (Inagaki N. and Katsuta K., Curr. Proteomics 1, 35-39, 2004)-based proteomics, to comprehensively analyze proteins, the expression of which increases in accordance with axon formation. The result was the identification of a novel protein (Singar) having a molecular weight of 57 kD. This molecule was analyzed further, leading to the findings that: (1) it is expressed specifically in the brain, peaking during four days to one week after birth, when axon formation is prominent; (2) strong enrichment of Singar was observed in the growth cones, which control neuritic elongation; (3) suppression of Singar expression by RNAi induces multiple axon formation in cultured neurons; and (4) there are at least two splicing variants for Singar, and the like, leading us to the present invention.

That is, the present invention includes the following industrially and medically useful inventions A) to G).

A) A method for inducing axon formation or elongation in a neuron by suppressing the expression or activity of Singar.

The term "Singar" implies, as described in detail below, a protein coded by a singar gene on a genome, including amino acid substitution-containing mutant proteins caused by multiple splicing variants, SNPs and the like.

Examples of methods for "suppressing expression or activity" of Singar include (1) a method for suppressing the Singar gene after transcription (for example, knockdown by RNAi as described below); (2) a method for selectively inhibiting or suppressing Singar gene transcription by reducing promoter activity or the like; (3) a method for specifically suppressing Singar protein expression by selectively inhibiting any processes of splicing, translation or post-translational modification; and (4) a method for inhibiting and/or suppressing Singar activity by administering agents having Singar protein inhibiting or suppressing activities (anti-Singar antibodies, other low molecular weight compounds, or the like), and the like, and combinations of these methods are also possible.

Further, a method for suppressing Singar expression or activity could be any that substantially reduces Singar expression levels (or activity) in a neuron, not requiring complete suppression of Singar expression (or activity).

B) A method for inducing axon formation or elongation according to Item A) above, wherein RNA that specifically suppresses Singar expression is introduced into a neuron.

The RNA (RNAi) may be siRNA (short interference RNA: also called "short interfering RNA", "small interfering RNA" or the like), an RNAi expression vector (also called "siRNA expression vector" or the like). The siRNA and the RNAi expression vectors can be designed based on the Singar gene sequence to be targeted following a known method (for example, see Ambion TechNotes 9 (1): 3-5 (2002), Proc. Natl.

Acad. Sci. USA 99 (8): 5515-5520 (2002), Proc. Natl. Acad. Sci. USA 99 (9): 6047-6052 (2002), Nature Biotechnology 20: 505-508 (2002) or the like). The RNAi expression vectors may be: (1) designed to express dsRNA inside the target cells, the dsRNA being a single RNA having an appropriate length of a hairpin structure; or (2) designed to express each sense strand and antisense strand, which pair in the target cells.

RNA can be introduced into neurons by general methods (for example, refer to Nature 411: 494-498 (2001), Science 296: 550-553 (2002) and the like), including those invented after the present invention.

C) An inducer for axon formation and/or elongation, comprising an RNA specifically suppressing Singar expression, or an RNAi expression vector constructed to express the RNA in a neuron.

The "RNAi expression vector" can be a virus vector, a plasmid, a phase or a cosmid, having a promoter functional in a neuron (for example, an RNA polymerase III type promoter such as U6, H1 promoter or the like, or RNA polymerase II type promoters, or the like) integrated upstream of the siRNA sequence to be expressed.

D) An inducer for axon formation or elongation according to C) above, wherein the RNA suppresses human-, rat- or mouse-derived Singar gene expression.

The human-, rat-, or mouse-derived Singar cDNA sequence and the amino acid sequence are each shown in SEQ ID NOs: 5 to 6, 7 to 10 and 1 to 4 of the Sequence Listing, from which information the target sequence can be determined, and siRNA and RNAi expression vectors capable of suppressing Singar protein expression can be designed and prepared.

E) A gene therapeutic agent for neuronal regeneration, comprising an RNA that specifically suppresses Singar expression, or an RNAi expression vector constructed to express the RNA in a neuron The above gene therapeutic agent can be used for axonal regeneration therapy for severed or degenerated neurons or nerve tissues.

F) A gene therapeutic agent for neuronal regeneration according to E) above, wherein the RNA suppresses human-, rat- or mouse-derived Singar gene expression.

G) A screening method for a nerve regeneration therapeutic agent, comprising the step of searching for a substance suppressing Singar expression or activity.

Examples of the screening method include, for example: (1) a method for searching for Singar-interacting (binding) substances using a binding assay such as an affinity column, Yeast-two-hybrid, immunoprecipitation or the like, and further screening for Singar activity-suppressing substances among them; (2) a method for searching for an endogenous substance, which interact (bind) with Singar in the same manner, and further screening for substances that inhibit the substance-Singar interaction; (3) a method for screening for a singer expression-reducing substance using Western blot or the like by administering a test substance to a neuron ; (4) a method for screening for a Singar expression- or activity-inhibiting substance using the induction of axon formation as an index after administering a test substance to a neuron and the like.

Effects of the Invention

The above Singar was found to have the effect of, as shown in the examples below, inducing multiple axon formation upon the suppression of its expression in a neuron, and the like. As such, Singar suppression induces axon formation, making it a target molecule for axonal regeneration therapy in the central nerves or peripheral nerves, which allows application in medical and pharmaceutical fields. Firstly, suppression of Singar expression promotes axon formation in a neuron. Thus, introduction of RNA that specifically inhibits Singar expression in the affected neurons or neural tissues of patients is considered to possibly induce axonal regeneration. Moreover, use of the screening method of the present invention allows, for example, Singar-interacting, Singar function- and/or activity-suppressing molecules to be found, making the molecules usable for developing therapeutic nerve regeneration agents.

BRIEF DESCRIPTION OF THE DRAWINGS

FIGS. 2 (a) to (c) show the results of analysis for the presence of Singar expression in various organs and its stage specific expression using an anti-Singar antibody. Results of (a) Singar expression in each organ: the brain, heart, liver, spleen, kidney, lung, skeletal muscle and placenta; (b) Singar expression from embryonic day 15 (E15) to adult in the rat brain; and (c) serial Singar expression in cultured neurons (from 12 hours to 28 days in culture) are shown.

FIGS. 3 (a) and (b) show Singar expression and its distribution in cultured hippocampal neurons analyzed by an anti-Singar antibody: (a) represents a general view of Singar-immunostained neurons (Singar is shown in green in the original); (b) shows an enlarged view around an axonal growth cone, the left panel representing Singar-immunostaining (shown in green in the original), the middle panel representing actin-immunostaining by an anti-actin antibody (shown in red in the original), the right panel representing a merged view of immunostaining by both Singar antibody and antibodies.

FIG. 4 shows a siRNA target sequence (SEQ ID NOS: 11-12, respectively in order of appearance) designed to suppress Singar gene expression and a scRNA sequence (SEQ ID NO: 13) used as a control.

BEST MODE FOR CARRYING OUT THE INVENTION

Specific embodiments of the present invention are explained below in detail with reference to the figures.

Figure 1:
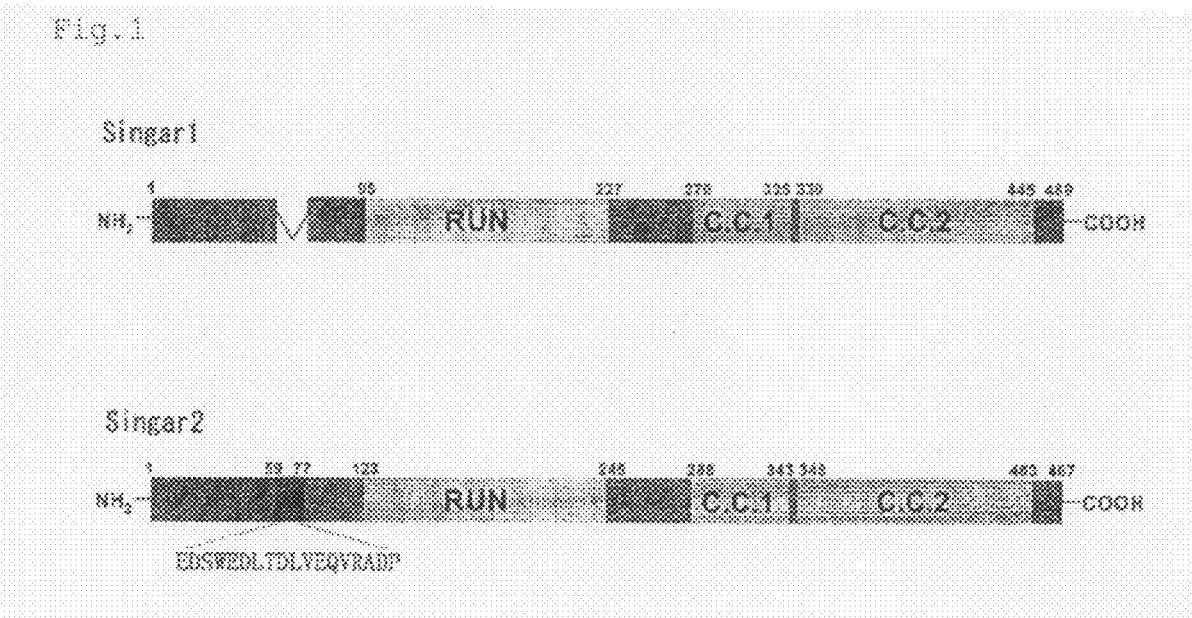
FIG. 1 is a schematic representation of the Singar structures (Singar1 and Singar2 (SEQ ID NO: 14)) revealed by this analysis. Each integer in the figure represents the position of each amino acid residue.

FIG. 1 represents the schematic structure of the Singar protein revealed by the analysis of the present inventors. There are at least two splicing variants of the Singar protein: Singar1 and Singar2. Here, the term "splicing variants" indicates proteins that are translated from different mRNA processed by alternative splicing after being transcribed from the same gene (Singar gene) on the genome. Singar1 with the shorter amino acid sequence consists of 469 full-length amino acids, while Singar2 with the longer amino acid sequence consists of 487 full-length amino acids. The difference in these is, as shown in FIG. 1, the presence of the $59^{th}$ to $76^{th}$ amino acid sequence (18 amino acids: EDSWEDLT-DLVEQVRADP) (SEQ ID NO: 14) in Singar2. Both Singar1 and Singar2 have a structure with one novel domain: RUN (Rap2 interacting protein 8, UNC-14, NESCA homology) domain, and two coiled-coil (C.C.1 and C.C.2 in the figure) domains.

As mentioned below, because both Singar1 and Singar2 are co-expressed in the brain, according to the present invention, it is preferable to control both Singar1 and Singar2. However, as long as axon formation or elongation can be induced and/or promoted, a method suppressing one of: Singar1 expression or activity; or, Singar2 expression or activity; may also be used.

SEQ ID NOs: 1 to 2 represent the cDNA and the amino acid sequences of mouse-derived Singar1. These sequences are disclosed at the DDBJ/EMBL/GenBank databases with Accession NO: "CT010404" (GI: 31542481). SEQ ID NOs: 3 to 4 represent the cDNA and the amino acid sequences of mouse-derived Singar2. These sequences are disclosed at the same databases with Accession NO: "BC058259" (GI: 34849578). SEQ ID NOs: 5 to 6 represent the cDNA and amino acid sequences of human-derived Singar1. These sequences are disclosed at the same databases with Accession NO: "BCO51716" (GI: 30704843). However, few Singar functions are disclosed at those databases.

SEQ ID NOs: 7 to 8 represent the cDNA and the amino acid sequences of rat-derived Singar1. These sequences are disclosed at the same databases with Accession NO: "BC089952" (GI: 58477176). On the other hand, SEQ ID NOs: 9 to 10 represent the cDNA sequence and the amino acid sequence of the rat-derived Singar2 determined by the present inventors. These rat-derived Singar2 gene and protein are a novel gene and a novel protein cloned by the present inventors for the first time.

According to the present invention, the term "Singar" includes not only the human-, mouse- and rat-derived Singars, but also includes those with partially different gene sequences by SNP and the like, and amino acid substitution. Other than mouse and rat, a method that suppresses the expression or activity of other experimentally usable mammalian-derived Singars to induce formation and elongation of axon may also be used.

Cloned rat-derived Singar was expressed to produce an anti-Singar antibody, and Singar expression was analyzed, giving the following findings (experimental procedures and the like are explained in detail with reference to the examples below).

(1) The presence of expression and stage-specific expression in each rat organ were investigated by Western blot analysis using an anti-Singar antibody, demonstrating brain-specific expression of Singar, and up-regulated expression during postnatal day 4 (P4) to week 1 (P7), when axon formation is prominent in the brain (FIGS. 2 (a) and (b)).

(2) After culturing, up-regulated expression was observed in cultured neurons during the period when axons are formed and elongated (FIG. 2 (c)).

(3) The phosphorylated form of Singar exists (FIG. 2 (c)), and it seems that the phosphorylation is regulating the Singar function.

(4) In cultured neurons prepared from embryonic day 18 rat hippocampus, strong Singar enrichment was observed in the elongating growth cones of axons, co-localized with actin filaments (FIG. 3). Other than being localized in growth cones, Singar also localized in cell bodies and dendrites.

Figure 6:
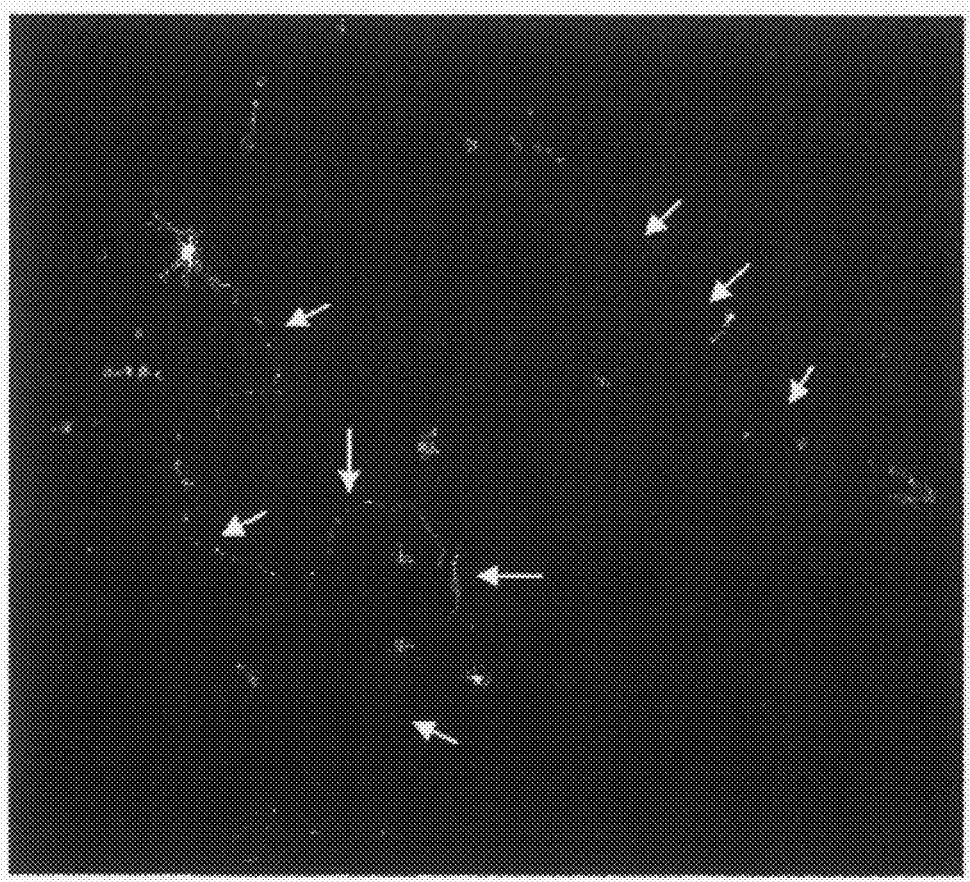
FIG. 6 shows multiple axons being formed by suppressing Singar expression in rat cultured hippocampal neurons. Arrows indicate axons. In the original, neurons were shown in green.
Figure 7:
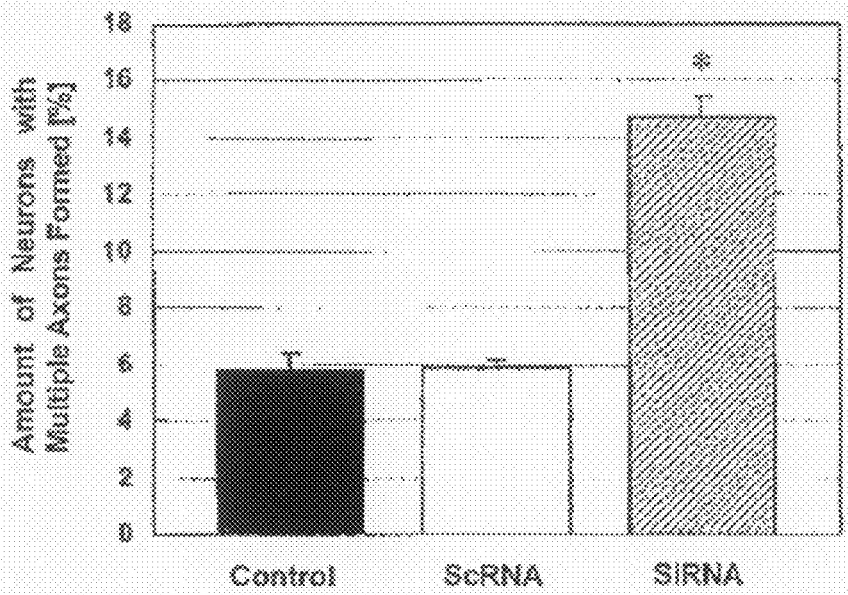
FIG. 7 is a graph demonstrating that the proportion of multiple axon formation was increased by suppressing Singar expression in rat cultured hippocampal neurons. In the figure, "Control" indicates that no RNAi was introduced, "ScRNA" that control scRNA was introduced, and "SiRNA" that RNAi was introduced. "*" indicates that significant differences exists between "SiRNA" and "Control"/"ScRNA".

(5) The suppression of Singar expression in cultured hippocampal neurons using RNAi induced multiple axon formation (FIGS. 6 and 7).

Furthermore, the present inventors previously developed and proposed a novel method for expressing excess amounts of nerve growth cone localized molecule: Shootin1, thereby inducing axon formation or elongation (refer to WO 2006/016429). This induction effect was reduced by co-expressing Singar.

From those results, it was demonstrated that Singar exists in axonal growth cones and the like, and plays important roles in axon formation. In particular, suppressing Singar expression resulted in the induction of axon formation, thus, suppression of Singar expression or activity can induce and/or promote axon formation or elongation in a neuron.

Examples of a method for suppressing Singar expression include, for example, as mentioned above, a method for intracellular expression of siRNA that specifically suppresses Singar expression is introduced into neurons using a vector such as a virus vector or the like. Such RNAi expression vectors can also be used as therapeutic nerve regeneration agents for regenerating damaged neurons. siRNA may be introduced into neurons either in vivo or ex vivo. Such in vivo methods, allowing effective and selective introduction of siRNA into affected neurons, can employ known carriers or drug delivery systems proposed to deliver vectors or nucleic acids to a particular part or a particular cell.

In the examples below, siRNA was directed against the target sequence shown in FIG. 4, and the siRNA was expressed intracellularly to suppress Singar protein expression; however, siRNA for suppressing Singar protein expression is not limited to this siRNA sequence. Other Singar protein suppressive siRNA sequences can also be designed from the Singar gene sequence as described before. According to the method of the present invention, Singar protein expression is not necessarily completely suppressed; substantial reduction in intracellular Singar protein expression is adequate. Moreover, the method of the present invention that suppresses Singar expression or activity to induce axon formation or elongation may also be used in combination with other methods for inducing axons (for example, a method for inducing axons using Shootin1, and the like).

Examples of other methods for suppressing Singar expression or activity include not only a method of introducing anti-Singar antisense oligonucleotides, ribozymes, antibodies or the like into neurons and the like, but also a method of administering a Singar expression- or activity-inhibiting substance to neurons. Therefore, a screening method for Singar expression- or activity-inhibiting substances is useful, and thereby included in the present invention.

The screening method of the present invention can employ various kinds of previously known methods for examining changes in gene or protein expression or protein activity and the like, and is not particularly limited. Other screening methods invented after the present invention may also be used. The present invention may employ any in vitro or in vivo screening method. Cell-free system screening can also be used. A Singar gene or protein may also be derived from a source other than human, such as rat, mouse or another animal. In silico screening using higher structural information on the Singar protein may also be used.

Examples of the screening method of the present invention include, as described above, (1) a method for searching for Singar-interacting (binding) substances and further screening for Singar activity-suppressing substances among the substances found, (2) a method for searching for Singar-interacting (binding) endogenous substances, and further screening for substances that inhibit the endogenous substance-Singar interaction, (3) a method for screening for a Singar expression-reducing substance using Western blot or the like by administering a test substance to a neuron, (4) a method for screening for a Singar expression- or activity-inhibiting substance using the induction of axon formation as an index after administering a test substance to a neuron and the like.

For example, Singar is considered to be regulated by phosphorylation, and dephosphorylation. Searching for such kinase- or phosphatase-Singar interaction-inhibiting substances is expected to allow effective screening for Singar activity-suppressing substances. Suppression of Singar expression in cultured neurons induced multiple axon formation (FIG. 6). Hence, the search for substances that cause similar morphological changes (induction of axon formation) in cultured neurons are also expected to allow effective screening for Singar expression- or activity-suppressing substances.

EXAMPLES

The present invention is described in detail below in reference to examples; however, the present invention is not limited to those examples.

Example 1

Cloning of Rat Singar Gene

The present inventors recently developed a high-sensitivity two-dimensional electrophoresis method (Inagaki N. and Katsuta K, Curr. Proteomics 1, 35-39, 2004).

Using this method, approximately 6,200 proteins from cultured rat hippocampal neurons were screened and 277 protein spots in which expression increases in accordance with nerve axon formation were detected.

Also, approximately 5,200 protein spots were screened in the same manner, and 200 protein spots concentrated in nerve axons were detected. One of the proteins detected by these two screening processes was analyzed with a MALDI-TOF MS (Mass Spectroscope). As a result of the analysis, a novel protein Singar (Singar1) 57 kD in molecular weight was identified, and a novel gene encoding the protein was cloned. The cDNA sequence of the Singar (Singar1) gene thus cloned and the amino acid sequence of the Singar (Singar1) protein encoded by the gene are shown in SEQ ID NOs: 9 to 10.

An analysis of information on the genome and the later-described immunoblotting analysis showed that there are two splicing variants of Singar protein, Singar1 and Singar2 (see FIG. 1). Further, as described above, the cDNA sequences and amino acid sequences of mouse-derived Singar (Singar1 and Singar2) and human-derived Singar (Singar1) were also identified.

Example 2

Analyses of Singar Tissue Expression in Rat Organs

Preparation and Purification of Anti-Singar Antibody
The GST-fusion protein of the rat Singar obtained by the foregoing cloning was expressed in *E. coli*, and purified using a Glutathione Sepharose 4B column. Afterwards, GST was cleaved and removed from the purified protein using protease. The obtained Singar was inoculated into a rabbit to prepare an antibody according to a routine procedure. The obtained antibody was column-purified with Singar serving as a ligand. The purified antibody was used for the following experiment.
Immunoblotting
Samples prepared from various organs of Wistar rats were treated with SDS, and 15 μg of each sample was separated using 10% polyacrylamide gel. The proteins were then transferred to a PVDF membrane, and Singar was detected using the above-mentioned anti-Singar antibody (at 1/1000 dilution), a HRP-labeled anti-rabbit IgG (at 1/2000 dilution), and ECL reagents (Amersham Biosciences). The detection found that Singar was specifically expressed in the brain, as shown in FIG. 2(*a*). As to the expression time, expression was relatively low in the embryonic period (E15, E18), and increased around postnatal day 4 (P4) to day 7 (P7). Singar was also expressed in the adult brain (FIG. 2(*b*)). The Singar expression time in cultured neuronal cells was also examined, with the result that the expression was low when there was no axon growth (after 12 hours cultivation), and increased around the time of elongation (after 62 hours (62 h) to Day 7 (7day)) (FIG. 2(*c*)).

As shown in FIG. 2, three bands were detected as a result of western blotting using the anti-Singar antibody. Among them, the top band designates Singar2 with a larger molecular weight. The two lower bands detected are Singar1, the upper band of which is assumed to designate a phosphorylated form of Singar1, as it disappears with phosphatase treatment.

Example 3

Analysis of Intracellular Distribution of Singar in Cultured Rat Hippocampal Neurons Preparation of Cultured Rat Hippocampal Neurons
Hippocampal neurons were dissociated from Hippocampi of E18 Wistar rat embryos by enzymatic digestion using papain. The obtained nerve cells were plated on coverslips coated with poly-D-lysine and laminin and cultured at 37° C., 5% $CO_2$, in a Neurobasal medium supplemented with a B-27 supplement, 1 mM glutamine, and 2.5 μM cytosine β-D-arabinofuranoside.
Immunostaining of Cultured Rat Hippocampal Neurons
Rat hippocampal neurons on the third day of cultivation were fixed on ice for 10 minutes with 3.7% formalin, and then subjected to membrane permeabilization for 10 minutes with −20° C. methanol. The cells were then incubated at 4° C. for an entire day using the anti-Singar antibody (at 1/5000 dilution) as the primary antibody, then incubated for one hour at room temperature using an ALEXA488-labeled anti-rabbit IgG antibody (at 1/1000 dilution) as the secondary antibody to visualize Singar. FIG. 3 shows the result. As shown in FIG. 3(*b*), in the cultured rat hippocampal neurons from the E18 Wistar rat embryo, significant Singar accumulation co-localized with actin filaments was seen in the growth cones on the tip of an elongating axon. Apart from the growth cones, Singar was also localized in the cell body and dendrites (FIG. 3(*a*)).

Example 4

Derivation of Nerve Axon Formation by Suppression of Singar Expression Using RNAi Some siRNAs were designed to suppress the expression of Singar. The target sequences for two of them were selected from 19 bases respectively from the 395th and the 846th bases from the initiating codon of rat Singar1 mRNA (FIG. 4). These target sequences were selected by the inventors of the present invention as a result of analysis of their similarity to known gene sequences, etc., based on the foregoing sequence information. Also, scRNA was created as a control. This scRNA encoded the same amino acid as that of the RNA corresponding to the second target sequence but differed in nucleotide sequence.

Figure 5:
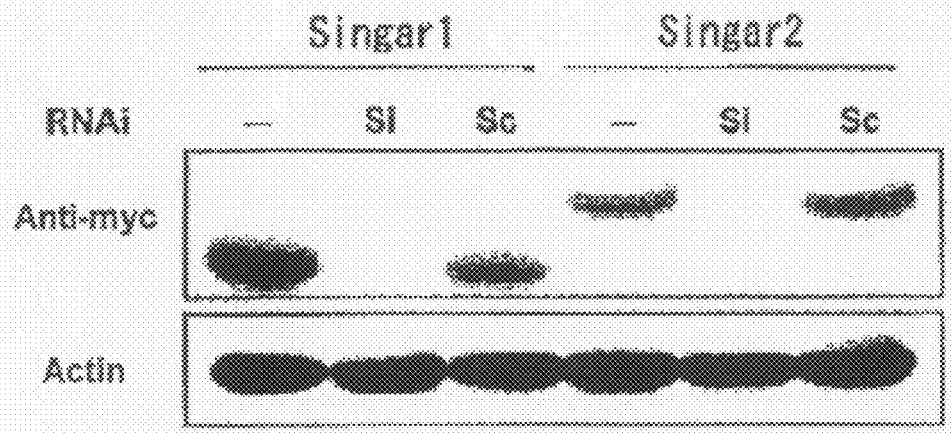
FIG. 5 shows Singar (Singar1 and Singar2) expression being suppressed by siRNA. Myc-tagged Singar1 and Singar2 are each expressed in human kidney-derived HEK293 cells to analyze the effect of RNAi introduction on their expression by Western blot using the anti-myc antibody. In the figures, "–" indicates that no RNAi was introduced, "Si" that RNAi was introduced, and "Sc" that scRNA was introduced as a control. In the experiment, actin expression was analyzed to confirm that equivalent amounts of protein were loaded. It was found that siRNA suppressed Singar1 and Singar2 expression, whereas scRNA as the control did not.

The Singar (Singar1 and Singar2) suppression effect in the cells given by the above-mentioned siRNA was examined by western blotting. FIG. 5 shows the result. In the experiment, Singar1 and Singar2 with myc tags were expressed in human-kidney-derived HEK293 cells. The change in the amount expressed due to the introduction of the above-mentioned siRNA was analyzed by western blotting using an anti-myc antibody (Anti-myc). The amount of actin expressed was analyzed using an anti-actin antibody to ensure uniform protein loading. In the figure, "−" denotes cells with no introduction of RNA, "Si" denotes cells provided with the above-mentioned siRNA, and "Sc" denotes cells provided with scRNA as a control. As shown in the figure, the amount of Singar1 and Singar2 expressed was suppressed by the siRNA, but not suppressed by the control scRNA.

Next, the foregoing siRNA was introduced into cultured rat hippocampal neurons using Lipofectamine 2000 (Invitrogen) according to the attached protocol to suppress Singar expression, thereby analyzing the influence of this siRNA introduction on nerve axon formation. The siRNA was introduced into the prepared segregated nerve cells, and the neuron cells were plated on coverslips for 6 days of cultivation. FIGS. 6 and 7 show the result.

As shown in FIG. 6, the suppression of Singar expression caused by the siRNA promoted the formation of multiple axons. FIG. 7 summarizes the experimental results. In the figure, "Control" denotes cells with no introduction of RNAi, "Sc RNA" denotes cells provided with the above-mentioned scRNA as a control, and "SiRNA" denotes cells provided with the siRNA. The introduction of siRNA significantly increased the rate of the formation of multiple axons.

Prior to the present invention, the inventors of the present invention developed a new method for promoting the formation or elongation of nerve cell axons by causing excessive expression of nerve growth cone localized molecule Shootin1 in nerve cells (see PCT International Publication No. WO 2006/016429). However, co-expression with Singar decreases this promotion effect.

These results showed that Singar exists in the growth cones or the like on the tip of an elongating axon, and plays an important role in nerve axon growth; particularly, because suppression of Singar expression promoted nerve axon formation, nerve axon formation or elongation can be induced or promoted by suppressing expression or activity of Singar.

Several theories can be deduced about the mechanism of the effects caused by Singar. One theory is that, according to the above-mentioned phosphorylation, Singar is under the functional control of phosphorylation via a signal transmission system in the nerve cells. Also, according to the above-mentioned co-localization with actin filaments, Singar is assumed to be involved in the formation or maintenance of the cytoskeleton. Further, since the phosphorylated Singar is often seen in axon growth cones, Singar is assumed to have a property of suppressing the formation or elongation of axons in the dendrites, but is inactivated in the axon growth cones by phosphorylation.

Example 5

Figure 8:
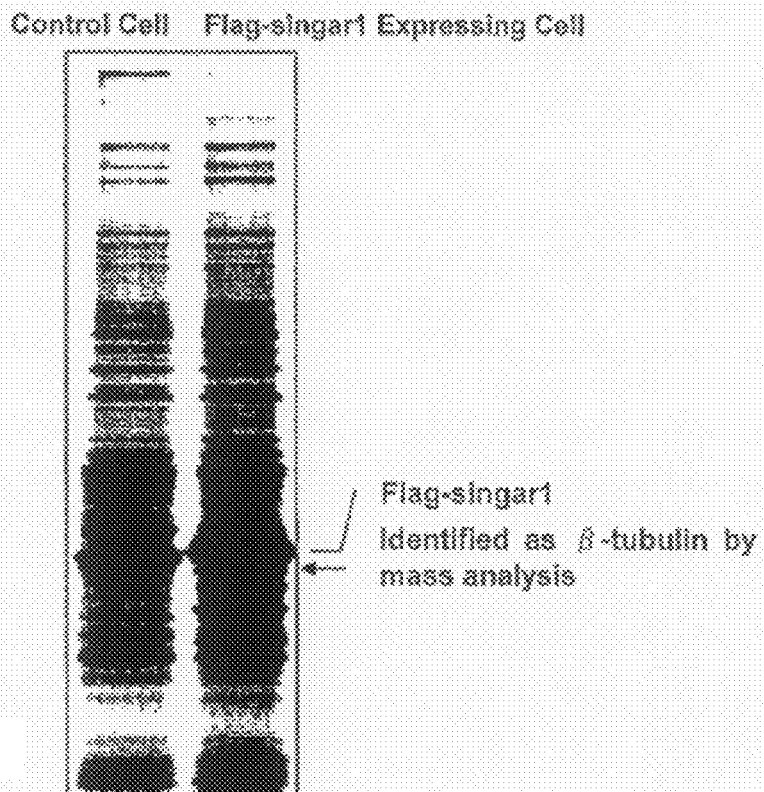
FIG. 8 shows the immunoprecipitation analysis of Singar1-interacting proteins. The arrow indicated Singar1-binding protein was identified as β-tubulin. The control cell is the HEK293 cell introduced with a control expression vector.

Screening of Proteins that Interact with Singar as Potential Substances for Suppressing Singar Search for Singar-bound Protein Using Immunoprecipitation FLAG-tagged Singar1 (Flag-Singar1) was expressed in HEK293 cells, and immunoprecipitation was performed using cell extracts with an anti-FLAG antibody. Thereafter, FLAG peptide was added to the precipitate to elute FLAG-Singar1. The Singar1-bound protein eluted therewith was separated by SDS-PAGE, and then silver stained (FIG. 8). One of the protein bands (denoted by the arrow) specifically found in the Singar1 expression cells was digested, then subjected to mass spectrometry. As a result, β-tubulin was identified as a Singar-bound protein.

INDUSTRIAL APPLICABILITY

As discussed above, the present invention can be utilized in the development of a novel neuronal regeneration technology. For example, as an effective remedy for damage to central and peripheral nerves caused by stroke or spinal cord injury, the present invention can be used at the establishment and developmental stages of neuronal regeneration technology. More specifically, the present invention has various industrial applications including the development of new medicines and clinical applications, such as use in new medical treatments to promote axon regeneration through the introduction of a vector such as a Singar expression-suppressing RNA virus vector, and use in the development of axon regeneration therapeutics by using Singar as a probe to screen Singar suppressing substances.

SEQUENCE LISTING FREE TEXT

SEQ ID NO. 1: cDNA sequence and amino acid sequence of mouse-derived Singar1

SEQ ID NO. 2: Amino acid sequence of mouse-derived Singar1

SEQ ID NO. 3: cDNA sequence and amino acid sequence of mouse-derived Singar2

SEQ ID NO. 4: Amino acid sequence of mouse-derived Singar2

SEQ ID NO. 5: cDNA sequence and amino acid sequence of human-derived Singar1

SEQ ID NO. 6: Amino acid sequence of human-derived Singar1

SEQ ID NO. 7: cDNA sequence and amino acid sequence of rat-derived Singar2

SEQ ID NO. 8: Amino acid sequence of rat-derived Singar1

SEQ ID NO. 9: cDNA sequence and amino acid sequence of rat-derived Singar2

SEQ ID NO. 10: Amino acid sequence of rat derived Singar2

SEQ ID NO. 11: Target sequence 1 of Singar gene expression-suppressing siRNA

SEQ ID NO. 12: Target sequence 2 of Singar gene expression-suppressing siRNA

SEQ ID NO. 13: scRNA sequence

The invention claimed is:

1. A method for inducing axon formation or elongation in a neuron, comprising suppressing expression or activity of Singar by introducing into a neuron an siRNA which is constructed to target the nucleotide sequence of SEQ ID NO: 11 or 12 wherein the Singar is from a human, rat or mouse.

2. The method of claim 1, wherein the suppressing expression or activity of Singar is carried out by introducing an RNAi expression vector which is constructed to express an RNA capable of specifically suppressing Singar expression.

3. The method according to claim 1, wherein the siRNA is constructed to target the nucleotide sequence of SEQ ID NO: 11.

4. The method according to claim 1, wherein the siRNA is constructed to target the nucleotide sequence of SEQ ID NO: 12.

* * * * *

SEQUENCE LISTING

<160> NUMBER OF SEQ ID NOS: 14

<210> SEQ ID NO 1
<211> LENGTH: 1410
<212> TYPE: DNA
<213> ORGANISM: Mus musculus
<220> FEATURE:
<221> NAME/KEY: CDS
<222> LOCATION: (1)..(1410)

<400> SEQUENCE: 1

| | | | | | | | | | | | | | | | | |
|---|---|---|---|---|---|---|---|---|---|---|---|---|---|---|---|---|
| atg | tct | gcc | ctg | acg | cct | ccg | act | gat | atg | cca | acc | ccc | acc | act | gac | 48 |
| Met | Ser | Ala | Leu | Thr | Pro | Pro | Thr | Asp | Met | Pro | Thr | Pro | Thr | Thr | Asp | |
| 1 | | | | 5 | | | | | 10 | | | | | 15 | | |

| aag | atc | aca | cag | gct | gcc | atg | gag | acc | atc | tac | ctt | tgc | aaa | ttc | cga | 96 |
|---|---|---|---|---|---|---|---|---|---|---|---|---|---|---|---|---|
| Lys | Ile | Thr | Gln | Ala | Ala | Met | Glu | Thr | Ile | Tyr | Leu | Cys | Lys | Phe | Arg | |
| | | | 20 | | | | | 25 | | | | | 30 | | | |

| gtg | tct | atg | gac | gga | gaa | tgg | ctc | tgc | ctt | cgg | gag | ctg | gat | gac | atc | 144 |
|---|---|---|---|---|---|---|---|---|---|---|---|---|---|---|---|---|
| Val | Ser | Met | Asp | Gly | Glu | Trp | Leu | Cys | Leu | Arg | Glu | Leu | Asp | Asp | Ile | |
| | | 35 | | | | | 40 | | | | | 45 | | | | |

| tcc | ctt | aca | ccc | gac | cca | gag | ccg | acc | cat | gaa | gat | ccc | aat | tat | ctc | 192 |
|---|---|---|---|---|---|---|---|---|---|---|---|---|---|---|---|---|
| Ser | Leu | Thr | Pro | Asp | Pro | Glu | Pro | Thr | His | Glu | Asp | Pro | Asn | Tyr | Leu | |
| 50 | | | | | 55 | | | | | 60 | | | | | | |

| atg | gct | aac | gaa | cgc | atg | aac | ctg | atg | aac | atg | gca | aag | ctg | agc | atc | 240 |
|---|---|---|---|---|---|---|---|---|---|---|---|---|---|---|---|---|
| Met | Ala | Asn | Glu | Arg | Met | Asn | Leu | Met | Asn | Met | Ala | Lys | Leu | Ser | Ile | |
| 65 | | | | 70 | | | | | 75 | | | | | 80 | | |

| aag | ggc | ttg | att | gaa | tcg | gct | ctg | aat | ctg | ggg | cgg | acc | ctg | gac | tct | 288 |
|---|---|---|---|---|---|---|---|---|---|---|---|---|---|---|---|---|
| Lys | Gly | Leu | Ile | Glu | Ser | Ala | Leu | Asn | Leu | Gly | Arg | Thr | Leu | Asp | Ser | |
| | | | | 85 | | | | | 90 | | | | | 95 | | |

| gac | tac | gca | cct | ctc | cag | cag | ttt | ttc | gtg | gtg | atg | gaa | cac | tgc | ctg | 336 |
|---|---|---|---|---|---|---|---|---|---|---|---|---|---|---|---|---|
| Asp | Tyr | Ala | Pro | Leu | Gln | Gln | Phe | Phe | Val | Val | Met | Glu | His | Cys | Leu | |
| | | | 100 | | | | | 105 | | | | | 110 | | | |

| aaa | cac | ggc | ttg | aaa | gcc | aag | aaa | act | ttt | ctt | gga | caa | aat | aaa | tcc | 384 |
|---|---|---|---|---|---|---|---|---|---|---|---|---|---|---|---|---|
| Lys | His | Gly | Leu | Lys | Ala | Lys | Lys | Thr | Phe | Leu | Gly | Gln | Asn | Lys | Ser | |
| | | 115 | | | | | 120 | | | | | 125 | | | | |

| ttc | tgg | ggg | cct | cta | gag | ctg | gtg | gag | aag | ctt | gtt | cca | gaa | gct | gca | 432 |
|---|---|---|---|---|---|---|---|---|---|---|---|---|---|---|---|---|
| Phe | Trp | Gly | Pro | Leu | Glu | Leu | Val | Glu | Lys | Leu | Val | Pro | Glu | Ala | Ala | |
| | | 130 | | | | | 135 | | | | | 140 | | | | |

| gaa | ata | aca | gcg | agt | gta | aaa | gac | ctc | cca | gga | ctc | aag | aca | cca | gtt | 480 |
|---|---|---|---|---|---|---|---|---|---|---|---|---|---|---|---|---|
| Glu | Ile | Thr | Ala | Ser | Val | Lys | Asp | Leu | Pro | Gly | Leu | Lys | Thr | Pro | Val | |
| 145 | | | | 150 | | | | | 155 | | | | | 160 | | |

| ggc | aga | gga | aga | gcc | tgg | ctt | cgg | ttg | gca | ttg | atg | caa | aag | aag | ctt | 528 |
|---|---|---|---|---|---|---|---|---|---|---|---|---|---|---|---|---|
| Gly | Arg | Gly | Arg | Ala | Trp | Leu | Arg | Leu | Ala | Leu | Met | Gln | Lys | Lys | Leu | |
| | | | | 165 | | | | | 170 | | | | | 175 | | |

| tct | gag | tat | atg | aaa | gcc | ttg | atc | aat | aag | aag | gaa | ctt | ctc | agt | gag | 576 |
|---|---|---|---|---|---|---|---|---|---|---|---|---|---|---|---|---|
| Ser | Glu | Tyr | Met | Lys | Ala | Leu | Ile | Asn | Lys | Lys | Glu | Leu | Leu | Ser | Glu | |
| | | | 180 | | | | | 185 | | | | | 190 | | | |

| ttc | tat | gaa | gtc | aat | gcc | ctc | atg | atg | gaa | gaa | gaa | gga | gct | att | atc | 624 |
|---|---|---|---|---|---|---|---|---|---|---|---|---|---|---|---|---|
| Phe | Tyr | Glu | Val | Asn | Ala | Leu | Met | Met | Glu | Glu | Glu | Gly | Ala | Ile | Ile | |
| | | 195 | | | | | 200 | | | | | 205 | | | | |

| gct | ggt | ctc | ctg | gtg | ggt | ctg | aat | gtc | atc | gat | gcc | aat | ttc | tgc | atg | 672 |
|---|---|---|---|---|---|---|---|---|---|---|---|---|---|---|---|---|
| Ala | Gly | Leu | Leu | Val | Gly | Leu | Asn | Val | Ile | Asp | Ala | Asn | Phe | Cys | Met | |
| | | 210 | | | | | 215 | | | | | 220 | | | | |

| aaa | gga | gaa | gac | ctg | gac | tct | cag | gtt | gga | gtt | ata | gat | ttt | tcg | atg | 720 |
|---|---|---|---|---|---|---|---|---|---|---|---|---|---|---|---|---|
| Lys | Gly | Glu | Asp | Leu | Asp | Ser | Gln | Val | Gly | Val | Ile | Asp | Phe | Ser | Met | |
| 225 | | | | 230 | | | | | 235 | | | | | 240 | | |

| tat | ctc | aaa | gat | gga | aac | agt | agt | aaa | ggt | agt | gaa | ggg | gat | gga | cag | 768 |
|---|---|---|---|---|---|---|---|---|---|---|---|---|---|---|---|---|
| Tyr | Leu | Lys | Asp | Gly | Asn | Ser | Ser | Lys | Gly | Ser | Glu | Gly | Asp | Gly | Gln | |
| | | | | 245 | | | | | 250 | | | | | 255 | | |

| att | act | gcg | atc | cta | gac | cag | aag | aac | tat | gta | gaa | gaa | ctc | aac | aga | 816 |
|---|---|---|---|---|---|---|---|---|---|---|---|---|---|---|---|---|

```
Ile Thr Ala Ile Leu Asp Gln Lys Asn Tyr Val Glu Glu Leu Asn Arg
            260                 265                 270 cat ctg aat gca act gta aac aac ctt cag aca aaa gta gat ctg tta    864
His Leu Asn Ala Thr Val Asn Asn Leu Gln Thr Lys Val Asp Leu Leu
            275                 280                 285 gaa aaa tcc aac act aaa ttg aca gaa gaa ctt gcc gtt gcc aac aac    912
Glu Lys Ser Asn Thr Lys Leu Thr Glu Glu Leu Ala Val Ala Asn Asn
            290                 295                 300 aga att att acc tta caa gaa gaa atg gaa cga gtt aaa gaa gaa agc    960
Arg Ile Ile Thr Leu Gln Glu Glu Met Glu Arg Val Lys Glu Glu Ser
305                 310                 315                 320 tcc tat cta ctg gaa tcc aat cgg aag ggt cct aaa caa gac aga act   1008
Ser Tyr Leu Leu Glu Ser Asn Arg Lys Gly Pro Lys Gln Asp Arg Thr
                325                 330                 335 gca gaa ggg caa gcg ctg agc gaa gcc aga aag cat cta aag gag gag   1056
Ala Glu Gly Gln Ala Leu Ser Glu Ala Arg Lys His Leu Lys Glu Glu
                340                 345                 350 aca cag tta aga ttg gat gtc gag aag gag ctg gag ctg cag atc agc   1104
Thr Gln Leu Arg Leu Asp Val Glu Lys Glu Leu Glu Leu Gln Ile Ser
                355                 360                 365 atg agg cag gag atg gaa ctg gct atg aag atg ctg gag aag gat gtc   1152
Met Arg Gln Glu Met Glu Leu Ala Met Lys Met Leu Glu Lys Asp Val
370                 375                 380 tgt gag aag cag gat gcc ctg gtg tct ctg cgg cag cag ctg gac gat   1200
Cys Glu Lys Gln Asp Ala Leu Val Ser Leu Arg Gln Gln Leu Asp Asp
385                 390                 395                 400 ctc cgg gct ctt aag cat gag ctc gcc ttt aaa ctg cag agt tca gac   1248
Leu Arg Ala Leu Lys His Glu Leu Ala Phe Lys Leu Gln Ser Ser Asp
                405                 410                 415 cta gga gtg aaa cag aaa agt gaa tta aac agt cgc ttg gaa gaa aag   1296
Leu Gly Val Lys Gln Lys Ser Glu Leu Asn Ser Arg Leu Glu Glu Lys
                420                 425                 430 acc aat cag atg gct gcc acc att aaa cag ctg gag caa agt gaa aaa   1344
Thr Asn Gln Met Ala Ala Thr Ile Lys Gln Leu Glu Gln Ser Glu Lys
                435                 440                 445 gat ttg gtg aaa cag gca aag acc tta aat agt gca gca aat aaa ctg   1392
Asp Leu Val Lys Gln Ala Lys Thr Leu Asn Ser Ala Ala Asn Lys Leu
450                 455                 460 atc cca aag cac cat taa                                            1410
Ile Pro Lys His His
465

<210> SEQ ID NO 2
<211> LENGTH: 469
<212> TYPE: PRT
<213> ORGANISM: Mus musculus

<400> SEQUENCE: 2

Met Ser Ala Leu Thr Pro Pro Thr Asp Met Pro Thr Pro Thr Thr Asp
1               5                   10                  15

Lys Ile Thr Gln Ala Ala Met Glu Thr Ile Tyr Leu Cys Lys Phe Arg
            20                  25                  30

Val Ser Met Asp Gly Glu Trp Leu Cys Leu Arg Glu Leu Asp Asp Ile
        35                  40                  45

Ser Leu Thr Pro Asp Pro Glu Pro Thr His Glu Asp Pro Asn Tyr Leu
    50                  55                  60

Met Ala Asn Glu Arg Met Asn Leu Met Asn Met Ala Lys Leu Ser Ile
65                  70                  75                  80

Lys Gly Leu Ile Glu Ser Ala Leu Asn Leu Gly Arg Thr Leu Asp Ser
                85                  90                  95
```

```
Asp Tyr Ala Pro Leu Gln Gln Phe Phe Val Val Met Glu His Cys Leu
            100                 105                 110
Lys His Gly Leu Lys Ala Lys Lys Thr Phe Leu Gly Gln Asn Lys Ser
        115                 120                 125
Phe Trp Gly Pro Leu Glu Leu Val Glu Lys Leu Val Pro Glu Ala Ala
130                 135                 140
Glu Ile Thr Ala Ser Val Lys Asp Leu Pro Gly Leu Lys Thr Pro Val
145                 150                 155                 160
Gly Arg Gly Arg Ala Trp Leu Arg Leu Ala Leu Met Gln Lys Lys Leu
                165                 170                 175
Ser Glu Tyr Met Lys Ala Leu Ile Asn Lys Lys Glu Leu Leu Ser Glu
            180                 185                 190
Phe Tyr Glu Val Asn Ala Leu Met Met Glu Glu Gly Ala Ile Ile
        195                 200                 205
Ala Gly Leu Leu Val Gly Leu Asn Val Ile Asp Ala Asn Phe Cys Met
    210                 215                 220
Lys Gly Glu Asp Leu Asp Ser Gln Val Gly Val Ile Asp Phe Ser Met
225                 230                 235                 240
Tyr Leu Lys Asp Gly Asn Ser Ser Lys Gly Ser Glu Gly Asp Gly Gln
                245                 250                 255
Ile Thr Ala Ile Leu Asp Gln Lys Asn Tyr Val Glu Glu Leu Asn Arg
            260                 265                 270
His Leu Asn Ala Thr Val Asn Asn Leu Gln Thr Lys Val Asp Leu Leu
        275                 280                 285
Glu Lys Ser Asn Thr Lys Leu Thr Glu Glu Leu Ala Val Ala Asn Asn
    290                 295                 300
Arg Ile Ile Thr Leu Gln Glu Glu Met Glu Arg Val Lys Glu Glu Ser
305                 310                 315                 320
Ser Tyr Leu Leu Glu Ser Asn Arg Lys Gly Pro Lys Gln Asp Arg Thr
                325                 330                 335
Ala Glu Gly Gln Ala Leu Ser Glu Ala Arg Lys His Leu Lys Glu Glu
            340                 345                 350
Thr Gln Leu Arg Leu Asp Val Glu Lys Glu Leu Glu Leu Gln Ile Ser
        355                 360                 365
Met Arg Gln Glu Met Glu Leu Ala Met Lys Met Leu Glu Lys Asp Val
    370                 375                 380
Cys Glu Lys Gln Asp Ala Leu Val Ser Leu Arg Gln Gln Leu Asp Asp
385                 390                 395                 400
Leu Arg Ala Leu Lys His Glu Leu Ala Phe Lys Leu Gln Ser Ser Asp
                405                 410                 415
Leu Gly Val Lys Gln Lys Ser Glu Leu Asn Ser Arg Leu Glu Glu Lys
            420                 425                 430
Thr Asn Gln Met Ala Ala Thr Ile Lys Gln Leu Glu Gln Ser Glu Lys
        435                 440                 445
Asp Leu Val Lys Gln Ala Lys Thr Leu Asn Ser Ala Ala Asn Lys Leu
    450                 455                 460
Ile Pro Lys His His
465

<210> SEQ ID NO 3
<211> LENGTH: 1464
<212> TYPE: DNA
<213> ORGANISM: Mus musculus
<220> FEATURE:
<221> NAME/KEY: CDS
```

<222> LOCATION: (1)..(1464)

<400> SEQUENCE: 3

| | | | | | | | | | | | | | | | | |
|---|---|---|---|---|---|---|---|---|---|---|---|---|---|---|---|---|
| atg | tct | gcc | ctg | acg | cct | ccg | act | gat | atg | cca | acc | ccc | acc | act | gac | 48 |
| Met | Ser | Ala | Leu | Thr | Pro | Pro | Thr | Asp | Met | Pro | Thr | Pro | Thr | Thr | Asp | |
| 1 | | | 5 | | | | | 10 | | | | | 15 | | | |
| aag | atc | aca | cag | gct | gcc | atg | gag | acc | atc | tac | ctt | tgc | aaa | ttc | cga | 96 |
| Lys | Ile | Thr | Gln | Ala | Ala | Met | Glu | Thr | Ile | Tyr | Leu | Cys | Lys | Phe | Arg | |
| | | | 20 | | | | | 25 | | | | | 30 | | | |
| gtg | tct | atg | gac | gga | gaa | tgg | ctc | tgc | ctt | cgg | gag | ctg | gat | gac | atc | 144 |
| Val | Ser | Met | Asp | Gly | Glu | Trp | Leu | Cys | Leu | Arg | Glu | Leu | Asp | Asp | Ile | |
| | | 35 | | | | | 40 | | | | | 45 | | | | |
| tcc | ctt | aca | ccc | gac | cca | gag | ccg | acc | cat | gaa | gac | tct | tgg | gag | gat | 192 |
| Ser | Leu | Thr | Pro | Asp | Pro | Glu | Pro | Thr | His | Glu | Asp | Ser | Trp | Glu | Asp | |
| | 50 | | | | | 55 | | | | | 60 | | | | | |
| ttg | aca | gat | ttg | gtg | gag | caa | gtg | cgt | gct | gac | cca | gaa | gat | ccc | aat | 240 |
| Leu | Thr | Asp | Leu | Val | Glu | Gln | Val | Arg | Ala | Asp | Pro | Glu | Asp | Pro | Asn | |
| 65 | | | | | 70 | | | | | 75 | | | | | 80 | |
| tat | ctc | atg | gct | aac | gaa | cgc | atg | aac | ctg | atg | aac | atg | gca | aag | ctg | 288 |
| Tyr | Leu | Met | Ala | Asn | Glu | Arg | Met | Asn | Leu | Met | Asn | Met | Ala | Lys | Leu | |
| | | | | 85 | | | | | 90 | | | | | 95 | | |
| agc | atc | aag | ggc | ttg | att | gaa | tcg | gct | ctg | aat | ctg | ggg | cgg | acc | ctg | 336 |
| Ser | Ile | Lys | Gly | Leu | Ile | Glu | Ser | Ala | Leu | Asn | Leu | Gly | Arg | Thr | Leu | |
| | | | 100 | | | | | 105 | | | | | 110 | | | |
| gac | tct | gac | tac | gca | cct | ctc | cag | cag | ttt | ttc | gtg | gtg | atg | gaa | cac | 384 |
| Asp | Ser | Asp | Tyr | Ala | Pro | Leu | Gln | Gln | Phe | Phe | Val | Val | Met | Glu | His | |
| | | 115 | | | | | 120 | | | | | 125 | | | | |
| tgc | ctg | aaa | cac | ggc | ttg | aaa | gcc | aag | aaa | act | ttt | ctt | gga | caa | aat | 432 |
| Cys | Leu | Lys | His | Gly | Leu | Lys | Ala | Lys | Lys | Thr | Phe | Leu | Gly | Gln | Asn | |
| | 130 | | | | | 135 | | | | | 140 | | | | | |
| aaa | tcc | ttc | tgg | ggg | cct | cta | gag | ctg | gtg | gag | aag | ctt | gtt | cca | gaa | 480 |
| Lys | Ser | Phe | Trp | Gly | Pro | Leu | Glu | Leu | Val | Glu | Lys | Leu | Val | Pro | Glu | |
| 145 | | | | | 150 | | | | | 155 | | | | | 160 | |
| gct | gca | gaa | ata | aca | gcg | agt | gta | aaa | gac | ctc | cca | gga | ctc | aag | aca | 528 |
| Ala | Ala | Glu | Ile | Thr | Ala | Ser | Val | Lys | Asp | Leu | Pro | Gly | Leu | Lys | Thr | |
| | | | | 165 | | | | | 170 | | | | | 175 | | |
| cca | gtt | ggc | aga | gga | aga | gcc | tgg | ctt | cgg | ttg | gca | ttg | atg | caa | aag | 576 |
| Pro | Val | Gly | Arg | Gly | Arg | Ala | Trp | Leu | Arg | Leu | Ala | Leu | Met | Gln | Lys | |
| | | | 180 | | | | | 185 | | | | | 190 | | | |
| aag | ctt | tct | gag | tat | atg | aaa | gcc | ttg | atc | aat | aag | aag | gaa | ctt | ctc | 624 |
| Lys | Leu | Ser | Glu | Tyr | Met | Lys | Ala | Leu | Ile | Asn | Lys | Lys | Glu | Leu | Leu | |
| | | 195 | | | | | 200 | | | | | 205 | | | | |
| agt | gag | ttc | tat | gaa | gtc | aat | gcc | ctc | atg | atg | gaa | gaa | gaa | gga | gct | 672 |
| Ser | Glu | Phe | Tyr | Glu | Val | Asn | Ala | Leu | Met | Met | Glu | Glu | Glu | Gly | Ala | |
| | 210 | | | | | 215 | | | | | 220 | | | | | |
| att | atc | gct | ggt | ctc | ctg | gtg | ggt | ctg | aat | gtc | atc | gat | gcc | aat | ttc | 720 |
| Ile | Ile | Ala | Gly | Leu | Leu | Val | Gly | Leu | Asn | Val | Ile | Asp | Ala | Asn | Phe | |
| 225 | | | | | 230 | | | | | 235 | | | | | 240 | |
| tgc | atg | aaa | gga | gaa | gac | ctg | gac | tct | cag | gtt | gga | gtt | ata | gat | ttt | 768 |
| Cys | Met | Lys | Gly | Glu | Asp | Leu | Asp | Ser | Gln | Val | Gly | Val | Ile | Asp | Phe | |
| | | | | 245 | | | | | 250 | | | | | 255 | | |
| tcg | atg | tat | ctc | aaa | gat | gga | aac | agt | agt | aaa | ggt | agt | gaa | ggg | gat | 816 |
| Ser | Met | Tyr | Leu | Lys | Asp | Gly | Asn | Ser | Ser | Lys | Gly | Ser | Glu | Gly | Asp | |
| | | | 260 | | | | | 265 | | | | | 270 | | | |
| gga | cag | att | act | gcg | atc | cta | gac | cag | aag | aac | tat | gta | gaa | gaa | ctc | 864 |
| Gly | Gln | Ile | Thr | Ala | Ile | Leu | Asp | Gln | Lys | Asn | Tyr | Val | Glu | Glu | Leu | |
| | | 275 | | | | | 280 | | | | | 285 | | | | |
| aac | aga | cat | ctg | aat | gca | act | gta | aac | aac | ctt | cag | aca | aaa | gta | gat | 912 |
| Asn | Arg | His | Leu | Asn | Ala | Thr | Val | Asn | Asn | Leu | Gln | Thr | Lys | Val | Asp | |
| | 290 | | | | | 295 | | | | | 300 | | | | | |

```
ctg tta gaa aaa tcc aac act aaa ttg aca gaa gaa ctt gcc gtt gcc    960
Leu Leu Glu Lys Ser Asn Thr Lys Leu Thr Glu Glu Leu Ala Val Ala
305                 310                 315                 320 aac aac aga att att acc tta caa gaa gaa atg gaa cga gtt aaa gaa   1008
Asn Asn Arg Ile Ile Thr Leu Gln Glu Glu Met Glu Arg Val Lys Glu
                325                 330                 335 gaa agc tcc tat cta ctg gaa tcc aat cgg aag ggt cct aaa caa gac   1056
Glu Ser Ser Tyr Leu Leu Glu Ser Asn Arg Lys Gly Pro Lys Gln Asp
            340                 345                 350 aga act gca gaa ggg caa gcg ctg agc gaa gcc aga aag cat cta aag   1104
Arg Thr Ala Glu Gly Gln Ala Leu Ser Glu Ala Arg Lys His Leu Lys
        355                 360                 365 gag gag aca cag tta aga ttg gat gtc gag aag gag ctg gag ctg cag   1152
Glu Glu Thr Gln Leu Arg Leu Asp Val Glu Lys Glu Leu Glu Leu Gln
    370                 375                 380 atc agc atg agg cag gag atg gaa ctg gct atg aag atg ctg gag aag   1200
Ile Ser Met Arg Gln Glu Met Glu Leu Ala Met Lys Met Leu Glu Lys
385                 390                 395                 400 gat gtc tgt gag aag cag gat gcc ctg gtg tct ctg cgg cag cag ctg   1248
Asp Val Cys Glu Lys Gln Asp Ala Leu Val Ser Leu Arg Gln Gln Leu
                405                 410                 415 gac gat ctc cgg gct ctt aag cat gag ctc gcc ttt aaa ctg cag agt   1296
Asp Asp Leu Arg Ala Leu Lys His Glu Leu Ala Phe Lys Leu Gln Ser
            420                 425                 430 tca gac cta gga gtg aaa cag aaa agt gaa tta aac agt cgc ttg gaa   1344
Ser Asp Leu Gly Val Lys Gln Lys Ser Glu Leu Asn Ser Arg Leu Glu
        435                 440                 445 gaa aag acc aat cag atg gct gcc acc att aaa cag ctg gag caa agt   1392
Glu Lys Thr Asn Gln Met Ala Ala Thr Ile Lys Gln Leu Glu Gln Ser
    450                 455                 460 gaa aaa gat ttg gtg aaa cag gca aag acc tta aat agt gca gca aat   1440
Glu Lys Asp Leu Val Lys Gln Ala Lys Thr Leu Asn Ser Ala Ala Asn
465                 470                 475                 480 aaa ctg atc cca aag cac cat taa                                   1464
Lys Leu Ile Pro Lys His His
                485

<210> SEQ ID NO 4
<211> LENGTH: 487
<212> TYPE: PRT
<213> ORGANISM: Mus musculus

<400> SEQUENCE: 4

Met Ser Ala Leu Thr Pro Pro Thr Asp Met Pro Thr Pro Thr Thr Asp
1               5                   10                  15

Lys Ile Thr Gln Ala Ala Met Glu Thr Ile Tyr Leu Cys Lys Phe Arg
            20                  25                  30

Val Ser Met Asp Gly Glu Trp Leu Cys Leu Arg Glu Leu Asp Asp Ile
        35                  40                  45

Ser Leu Thr Pro Asp Pro Glu Pro Thr His Glu Asp Ser Trp Glu Asp
    50                  55                  60

Leu Thr Asp Leu Val Glu Gln Val Arg Ala Asp Pro Glu Asp Pro Asn
65                  70                  75                  80

Tyr Leu Met Ala Asn Glu Arg Met Asn Leu Met Asn Met Ala Lys Leu
                85                  90                  95

Ser Ile Lys Gly Leu Ile Glu Ser Ala Leu Asn Leu Gly Arg Thr Leu
            100                 105                 110

Asp Ser Asp Tyr Ala Pro Leu Gln Gln Phe Phe Val Val Met Glu His
        115                 120                 125
```

```
Cys Leu Lys His Gly Leu Lys Ala Lys Lys Thr Phe Leu Gly Gln Asn
130                 135                 140

Lys Ser Phe Trp Gly Pro Leu Glu Leu Val Glu Lys Leu Val Pro Glu
145                 150                 155                 160

Ala Ala Glu Ile Thr Ala Ser Val Lys Asp Leu Pro Gly Leu Lys Thr
                165                 170                 175

Pro Val Gly Arg Gly Arg Ala Trp Leu Arg Leu Ala Leu Met Gln Lys
            180                 185                 190

Lys Leu Ser Glu Tyr Met Lys Ala Leu Ile Asn Lys Lys Glu Leu Leu
        195                 200                 205

Ser Glu Phe Tyr Glu Val Asn Ala Leu Met Met Glu Glu Gly Ala
210                 215                 220

Ile Ile Ala Gly Leu Leu Val Gly Leu Asn Val Ile Asp Ala Asn Phe
225                 230                 235                 240

Cys Met Lys Gly Glu Asp Leu Asp Ser Gln Val Gly Val Ile Asp Phe
                245                 250                 255

Ser Met Tyr Leu Lys Asp Gly Asn Ser Ser Lys Gly Ser Glu Gly Asp
            260                 265                 270

Gly Gln Ile Thr Ala Ile Leu Asp Gln Lys Asn Tyr Val Glu Leu
        275                 280                 285

Asn Arg His Leu Asn Ala Thr Val Asn Asn Leu Gln Thr Lys Val Asp
290                 295                 300

Leu Leu Glu Lys Ser Asn Thr Lys Leu Thr Glu Glu Leu Ala Val Ala
305                 310                 315                 320

Asn Asn Arg Ile Ile Thr Leu Gln Glu Glu Met Glu Arg Val Lys Glu
                325                 330                 335

Glu Ser Ser Tyr Leu Leu Glu Ser Asn Arg Lys Gly Pro Lys Gln Asp
            340                 345                 350

Arg Thr Ala Glu Gly Gln Ala Leu Ser Glu Ala Arg Lys His Leu Lys
        355                 360                 365

Glu Glu Thr Gln Leu Arg Leu Asp Val Glu Lys Glu Leu Glu Leu Gln
370                 375                 380

Ile Ser Met Arg Gln Glu Met Glu Leu Ala Met Lys Met Leu Glu Lys
385                 390                 395                 400

Asp Val Cys Glu Lys Gln Asp Ala Leu Val Ser Leu Arg Gln Gln Leu
                405                 410                 415

Asp Asp Leu Arg Ala Leu Lys His Glu Leu Ala Phe Lys Leu Gln Ser
            420                 425                 430

Ser Asp Leu Gly Val Lys Gln Lys Ser Glu Leu Asn Ser Arg Leu Glu
        435                 440                 445

Glu Lys Thr Asn Gln Met Ala Thr Ile Lys Gln Leu Glu Gln Ser
450                 455                 460

Glu Lys Asp Leu Val Lys Gln Ala Lys Thr Leu Asn Ser Ala Ala Asn
465                 470                 475                 480

Lys Leu Ile Pro Lys His His
                485

<210> SEQ ID NO 5
<211> LENGTH: 1410
<212> TYPE: DNA
<213> ORGANISM: Homo sapiens
<220> FEATURE:
<221> NAME/KEY: CDS
<222> LOCATION: (1)..(1410)

<400> SEQUENCE: 5
```

```
atg tct gct ctg acg cct ccg acc gat atg cca acc ccc acc act gac    48
Met Ser Ala Leu Thr Pro Pro Thr Asp Met Pro Thr Pro Thr Thr Asp
1               5                   10                  15 aag atc aca cag gct gcc atg gag acc atc tac ctt tgc aaa ttc cga    96
Lys Ile Thr Gln Ala Ala Met Glu Thr Ile Tyr Leu Cys Lys Phe Arg
            20                  25                  30 gtg tcc atg gat gga gaa tgg ctc tgc ctg cga gag ctg gat gac atc   144
Val Ser Met Asp Gly Glu Trp Leu Cys Leu Arg Glu Leu Asp Asp Ile
        35                  40                  45 tca ctt aca cct gac cca gag cct acc cat gaa gat cct aat tat ctc   192
Ser Leu Thr Pro Asp Pro Glu Pro Thr His Glu Asp Pro Asn Tyr Leu
50                  55                  60 atg gct aat gaa cgc atg aac ctc atg aac atg gcc aag ctg agt atc   240
Met Ala Asn Glu Arg Met Asn Leu Met Asn Met Ala Lys Leu Ser Ile
65              70                  75                  80 aag ggc ttg att gaa tca gct ctg aac ctg ggg agg act ctt gac tct   288
Lys Gly Leu Ile Glu Ser Ala Leu Asn Leu Gly Arg Thr Leu Asp Ser
                85                  90                  95 gac tat gca cct ctc cag caa ttc ttt gtg gtg atg gag cac tgt ctg   336
Asp Tyr Ala Pro Leu Gln Gln Phe Phe Val Val Met Glu His Cys Leu
            100                 105                 110 aaa cat ggc ttg aaa gct aaa aaa act ttt ctc gga caa aat aaa tcc   384
Lys His Gly Leu Lys Ala Lys Lys Thr Phe Leu Gly Gln Asn Lys Ser
        115                 120                 125 ttc tgg ggg cct cta gaa ctg gta gaa aag ctt gtt cca gaa gcc gca   432
Phe Trp Gly Pro Leu Glu Leu Val Glu Lys Leu Val Pro Glu Ala Ala
130                 135                 140 gag ata aca gca agt gtt aaa gat ctt cca gga ctt aag aca cca gta   480
Glu Ile Thr Ala Ser Val Lys Asp Leu Pro Gly Leu Lys Thr Pro Val
145                 150                 155                 160 ggt aga gga aga gcc tgg ctt cgt ttg gca tta atg caa aag aaa ctt   528
Gly Arg Gly Arg Ala Trp Leu Arg Leu Ala Leu Met Gln Lys Lys Leu
                165                 170                 175 tca gaa tat atg aaa gct ttg atc aat aag aaa gaa ctt ctc agt gaa   576
Ser Glu Tyr Met Lys Ala Leu Ile Asn Lys Lys Glu Leu Leu Ser Glu
            180                 185                 190 ttc tac gaa ccc aat gcc ctc atg atg gaa gaa gaa gga gcc ata att   624
Phe Tyr Glu Pro Asn Ala Leu Met Met Glu Glu Glu Gly Ala Ile Ile
        195                 200                 205 gct ggt ctg ttg gtg ggt ctg aat gtc att gat gcc aat ttc tgt atg   672
Ala Gly Leu Leu Val Gly Leu Asn Val Ile Asp Ala Asn Phe Cys Met
    210                 215                 220 aaa gga gaa gac ttg gac tct cag gtt gga gtt ata gat ttt tca atg   720
Lys Gly Glu Asp Leu Asp Ser Gln Val Gly Val Ile Asp Phe Ser Met
225                 230                 235                 240 tat ctc aag gac ggg aac agc agt aaa ggt act gaa gga gac ggt cag   768
Tyr Leu Lys Asp Gly Asn Ser Ser Lys Gly Thr Glu Gly Asp Gly Gln
                245                 250                 255 att act gca att ctg gac cag aag aac tat gta gaa gaa ctg aac aga   816
Ile Thr Ala Ile Leu Asp Gln Lys Asn Tyr Val Glu Glu Leu Asn Arg
            260                 265                 270 cat ttg aat gct act gta aac aac ctt cag gca aaa gta gat gca tta   864
His Leu Asn Ala Thr Val Asn Asn Leu Gln Ala Lys Val Asp Ala Leu
        275                 280                 285 gaa aaa tcc aac act aaa ctg aca gag gag ctt gca gtt gca aac aac   912
Glu Lys Ser Asn Thr Lys Leu Thr Glu Glu Leu Ala Val Ala Asn Asn
    290                 295                 300 agg atc att acc tta caa gaa gaa atg gaa cga gtt aaa gag gaa agt   960
Arg Ile Ile Thr Leu Gln Glu Glu Met Glu Arg Val Lys Glu Glu Ser
305                 310                 315                 320
```

```
tcc tac ata ctg gaa tcc aat cgg aag ggt ccc aag caa gac aga act     1008
Ser Tyr Ile Leu Glu Ser Asn Arg Lys Gly Pro Lys Gln Asp Arg Thr
            325                 330                 335 gca gaa ggg caa gca cta agt gaa gca aga aag cat tta aaa gaa gag     1056
Ala Glu Gly Gln Ala Leu Ser Glu Ala Arg Lys His Leu Lys Glu Glu
        340                 345                 350 aca caa tta cga ttg gat gtt gag aaa gaa ctg gag atg cag atc agc     1104
Thr Gln Leu Arg Leu Asp Val Glu Lys Glu Leu Glu Met Gln Ile Ser
    355                 360                 365 atg agg cag gag atg gaa ttg gct atg aag atg ctg gag aag gat gtc     1152
Met Arg Gln Glu Met Glu Leu Ala Met Lys Met Leu Glu Lys Asp Val
370                 375                 380 tgt gag aag cag gat gcc ctg gta tct ctt cgg cag cag ctg gat gac     1200
Cys Glu Lys Gln Asp Ala Leu Val Ser Leu Arg Gln Gln Leu Asp Asp
385                 390                 395                 400 ctc aga gct ctc aag cat gaa ctt gcc ttt aag ctg cag agt tca gac     1248
Leu Arg Ala Leu Lys His Glu Leu Ala Phe Lys Leu Gln Ser Ser Asp
            405                 410                 415 tta gga gta aaa cag aaa agt gaa cta aac agt cgc ttg gaa gag aag     1296
Leu Gly Val Lys Gln Lys Ser Glu Leu Asn Ser Arg Leu Glu Glu Lys
        420                 425                 430 act aat cag atg gct gct acc att aaa caa ctt gaa caa agt gaa aag     1344
Thr Asn Gln Met Ala Ala Thr Ile Lys Gln Leu Glu Gln Ser Glu Lys
    435                 440                 445 gat ttg gtg aaa cag gca aag acc tta aat agt gca gca aat aaa ctg     1392
Asp Leu Val Lys Gln Ala Lys Thr Leu Asn Ser Ala Ala Asn Lys Leu
450                 455                 460 atc cca aaa cat cat tag                                              1410
Ile Pro Lys His His
465
```

<210> SEQ ID NO 6
<211> LENGTH: 469
<212> TYPE: PRT
<213> ORGANISM: Homo sapiens

<400> SEQUENCE: 6

```
Met Ser Ala Leu Thr Pro Pro Thr Asp Met Pro Thr Pro Thr Thr Asp
1               5                   10                  15

Lys Ile Thr Gln Ala Ala Met Glu Thr Ile Tyr Leu Cys Lys Phe Arg
            20                  25                  30

Val Ser Met Asp Gly Glu Trp Leu Cys Leu Arg Glu Leu Asp Asp Ile
        35                  40                  45

Ser Leu Thr Pro Asp Pro Glu Pro Thr His Glu Asp Pro Asn Tyr Leu
    50                  55                  60

Met Ala Asn Glu Arg Met Asn Leu Met Asn Met Ala Lys Leu Ser Ile
65                  70                  75                  80

Lys Gly Leu Ile Glu Ser Ala Leu Asn Leu Gly Arg Thr Leu Asp Ser
                85                  90                  95

Asp Tyr Ala Pro Leu Gln Gln Phe Phe Val Val Met Glu His Cys Leu
            100                 105                 110

Lys His Gly Leu Lys Ala Lys Lys Thr Phe Leu Gly Gln Asn Lys Ser
        115                 120                 125

Phe Trp Gly Pro Leu Glu Leu Val Glu Lys Leu Val Pro Glu Ala Ala
    130                 135                 140

Glu Ile Thr Ala Ser Val Lys Asp Leu Pro Gly Leu Lys Thr Pro Val
145                 150                 155                 160

Gly Arg Gly Arg Ala Trp Leu Arg Leu Ala Leu Met Gln Lys Lys Leu
                165                 170                 175
```

```
Ser Glu Tyr Met Lys Ala Leu Ile Asn Lys Lys Glu Leu Leu Ser Glu
            180                 185                 190

Phe Tyr Glu Pro Asn Ala Leu Met Met Glu Glu Gly Ala Ile Ile
        195                 200                 205

Ala Gly Leu Leu Val Gly Leu Asn Val Ile Asp Ala Asn Phe Cys Met
210                 215                 220

Lys Gly Glu Asp Leu Asp Ser Gln Val Gly Val Ile Asp Phe Ser Met
225                 230                 235                 240

Tyr Leu Lys Asp Gly Asn Ser Ser Lys Gly Thr Glu Gly Asp Gly Gln
                245                 250                 255

Ile Thr Ala Ile Leu Asp Gln Lys Asn Tyr Val Glu Glu Leu Asn Arg
            260                 265                 270

His Leu Asn Ala Thr Val Asn Asn Leu Gln Ala Lys Val Asp Ala Leu
        275                 280                 285

Glu Lys Ser Asn Thr Lys Leu Thr Glu Glu Leu Ala Val Ala Asn Asn
    290                 295                 300

Arg Ile Ile Thr Leu Gln Glu Glu Met Glu Arg Val Lys Glu Glu Ser
305                 310                 315                 320

Ser Tyr Ile Leu Glu Ser Asn Arg Lys Gly Pro Lys Gln Asp Arg Thr
                325                 330                 335

Ala Glu Gly Gln Ala Leu Ser Glu Ala Arg Lys His Leu Lys Glu Glu
            340                 345                 350

Thr Gln Leu Arg Leu Asp Val Glu Lys Glu Leu Glu Met Gln Ile Ser
        355                 360                 365

Met Arg Gln Glu Met Glu Leu Ala Met Lys Met Leu Glu Lys Asp Val
    370                 375                 380

Cys Glu Lys Gln Asp Ala Leu Val Ser Leu Arg Gln Gln Leu Asp Asp
385                 390                 395                 400

Leu Arg Ala Leu Lys His Glu Leu Ala Phe Lys Leu Gln Ser Ser Asp
                405                 410                 415

Leu Gly Val Lys Gln Lys Ser Glu Leu Asn Ser Arg Leu Glu Glu Lys
            420                 425                 430

Thr Asn Gln Met Ala Ala Thr Ile Lys Gln Leu Glu Gln Ser Glu Lys
        435                 440                 445

Asp Leu Val Lys Gln Ala Lys Thr Leu Asn Ser Ala Ala Asn Lys Leu
    450                 455                 460

Ile Pro Lys His His
465

<210> SEQ ID NO 7
<211> LENGTH: 1410
<212> TYPE: DNA
<213> ORGANISM: Rattus norvegicus
<220> FEATURE:
<221> NAME/KEY: CDS
<222> LOCATION: (1)..(1410)

<400> SEQUENCE: 7 atg tct gcc ctg acg cct ccg act gat atg cca acc ccc acc act gac     48
Met Ser Ala Leu Thr Pro Pro Thr Asp Met Pro Thr Pro Thr Thr Asp
1               5                   10                  15 aag ata acc cag gct gcc atg gag acc atc tac ctc tgc aaa ttc cgg     96
Lys Ile Thr Gln Ala Ala Met Glu Thr Ile Tyr Leu Cys Lys Phe Arg
            20                  25                  30 gtg tct atg gat gga gaa tgg ctc tgc ctt cga gag ctg gat gac atc    144
Val Ser Met Asp Gly Glu Trp Leu Cys Leu Arg Glu Leu Asp Asp Ile
        35                  40                  45
```

| | | | | | | | | | | | | | | | |
|---|---|---|---|---|---|---|---|---|---|---|---|---|---|---|---|
| tcc | ctt | aca | cct | gac | cca | gag | cct | acc | cat | gaa | gat | cct | aat | tat | ctc | 192 |
| Ser | Leu | Thr | Pro | Asp | Pro | Glu | Pro | Thr | His | Glu | Asp | Pro | Asn | Tyr | Leu |
| | 50 | | | | 55 | | | | | 60 | | | | | |

```
tcc ctt aca cct gac cca gag cct acc cat gaa gat cct aat tat ctc    192
Ser Leu Thr Pro Asp Pro Glu Pro Thr His Glu Asp Pro Asn Tyr Leu
     50              55                  60 atg gct aac gag cgc atg aac ctg atg aac atg gcg aag ctg agc atc    240
Met Ala Asn Glu Arg Met Asn Leu Met Asn Met Ala Lys Leu Ser Ile
 65              70                  75                      80 aag ggc ttg att gag tcg gct ctg aac ctg ggg cgg acc ctg gac tct    288
Lys Gly Leu Ile Glu Ser Ala Leu Asn Leu Gly Arg Thr Leu Asp Ser
                     85                  90                  95 gac tac gca cct ctc cag cag ttc ttc gtg gtg atg gaa cac tgc ctg    336
Asp Tyr Ala Pro Leu Gln Gln Phe Phe Val Val Met Glu His Cys Leu
             100                 105                 110 aaa cat ggc ttg aaa gcc aag aaa act ttt ctt gga caa aat aag tcc    384
Lys His Gly Leu Lys Ala Lys Lys Thr Phe Leu Gly Gln Asn Lys Ser
         115                 120                 125 ttc tgg ggt cct cta gag ctg gta gaa aag ctt gtt cca gaa gct gca    432
Phe Trp Gly Pro Leu Glu Leu Val Glu Lys Leu Val Pro Glu Ala Ala
130                 135                 140 gag ata aca gca agt gta aaa gat ctc cca gga ctc aag aca cca gtt    480
Glu Ile Thr Ala Ser Val Lys Asp Leu Pro Gly Leu Lys Thr Pro Val
145                 150                 155                 160 ggc aga gga aga gcc tgg ctt cgg ttg gca tta atg caa aag aag ctt    528
Gly Arg Gly Arg Ala Trp Leu Arg Leu Ala Leu Met Gln Lys Lys Leu
                 165                 170                 175 tct gag tac atg aag gcc ttg atc aat aag aag gaa ctt ctc agt gag    576
Ser Glu Tyr Met Lys Ala Leu Ile Asn Lys Lys Glu Leu Leu Ser Glu
             180                 185                 190 ttc tat gaa gcc aat gct ctc atg atg gaa gaa gaa ggc gca att att    624
Phe Tyr Glu Ala Asn Ala Leu Met Met Glu Glu Glu Gly Ala Ile Ile
         195                 200                 205 gct ggc ctc ctg gtc ggt ctg aat gtc atc gat gcc aat ttc tgc atg    672
Ala Gly Leu Leu Val Gly Leu Asn Val Ile Asp Ala Asn Phe Cys Met
210                 215                 220 aaa gga gaa gac ctg gac tct cag gtt ggc gtt ata gac ttt tca atg    720
Lys Gly Glu Asp Leu Asp Ser Gln Val Gly Val Ile Asp Phe Ser Met
225                 230                 235                 240 tat ctc aaa gat ggg aac agc agt aaa ggc agt gaa ggg gat gga cag    768
Tyr Leu Lys Asp Gly Asn Ser Ser Lys Gly Ser Glu Gly Asp Gly Gln
                 245                 250                 255 att act gcg att ctg gac cag aaa aac tat gta gaa gaa ctc aac aga    816
Ile Thr Ala Ile Leu Asp Gln Lys Asn Tyr Val Glu Glu Leu Asn Arg
             260                 265                 270 cat ctg aat gct act gta aac aac ctt cag gca aaa gta gat gcg tta    864
His Leu Asn Ala Thr Val Asn Asn Leu Gln Ala Lys Val Asp Ala Leu
         275                 280                 285 gaa aaa tcc aac acg aaa ttg aca gag gaa ctt gcc gtc gcc aac aac    912
Glu Lys Ser Asn Thr Lys Leu Thr Glu Glu Leu Ala Val Ala Asn Asn
290                 295                 300 aga att att acc tta caa gaa gaa atg gaa cgg gtt aaa gaa gaa agt    960
Arg Ile Ile Thr Leu Gln Glu Glu Met Glu Arg Val Lys Glu Glu Ser
305                 310                 315                 320 tcc tat cta ctg gaa tcc aat cgg aag ggt cct aag caa gac aga act    1008
Ser Tyr Leu Leu Glu Ser Asn Arg Lys Gly Pro Lys Gln Asp Arg Thr
                 325                 330                 335 gca gaa ggg caa gcg ctg agc gaa gcc aga aag cat cta aag gag gag    1056
Ala Glu Gly Gln Ala Leu Ser Glu Ala Arg Lys His Leu Lys Glu Glu
             340                 345                 350 aca cag tta cga ttg gac gtt gaa aag gag ctg gag ctg cag atc agc    1104
Thr Gln Leu Arg Leu Asp Val Glu Lys Glu Leu Glu Leu Gln Ile Ser
         355                 360                 365
```

```
atg agg cag gag atg gaa ctg gct atg aag atg ctg gag aag gat gtc      1152
Met Arg Gln Glu Met Glu Leu Ala Met Lys Met Leu Glu Lys Asp Val
370                 375                 380 tgt gag aag cag gat gcc ctg gtg tcc ctg cgg cag cag ctg gat gat      1200
Cys Glu Lys Gln Asp Ala Leu Val Ser Leu Arg Gln Gln Leu Asp Asp
385                 390                 395                 400 ctc cga gct ctt aaa cac gag ctt gcc ttt aag ctg cag agt tca gac      1248
Leu Arg Ala Leu Lys His Glu Leu Ala Phe Lys Leu Gln Ser Ser Asp
            405                 410                 415 cta gga gtg aaa cag aaa agt gaa tta aac agt cgc ttg gaa gag aag      1296
Leu Gly Val Lys Gln Lys Ser Glu Leu Asn Ser Arg Leu Glu Glu Lys
        420                 425                 430 acc aat cag atg gct gcc acc att aaa cag ctg gag caa agt gaa aaa      1344
Thr Asn Gln Met Ala Ala Thr Ile Lys Gln Leu Glu Gln Ser Glu Lys
    435                 440                 445 gat ttg gtg aaa cag gca aag acc tta aat agt gca gca aat aaa ctg      1392
Asp Leu Val Lys Gln Ala Lys Thr Leu Asn Ser Ala Ala Asn Lys Leu
450                 455                 460 atc cca aaa cat cat taa                                              1410
Ile Pro Lys His His
465
```

<210> SEQ ID NO 8
<211> LENGTH: 469
<212> TYPE: PRT
<213> ORGANISM: Rattus norvegicus

<400> SEQUENCE: 8

```
Met Ser Ala Leu Thr Pro Pro Thr Asp Met Pro Thr Pro Thr Thr Asp
1               5                   10                  15

Lys Ile Thr Gln Ala Ala Met Glu Thr Ile Tyr Leu Cys Lys Phe Arg
            20                  25                  30

Val Ser Met Asp Gly Glu Trp Leu Cys Leu Arg Glu Leu Asp Asp Ile
        35                  40                  45

Ser Leu Thr Pro Asp Pro Glu Pro Thr His Glu Asp Pro Asn Tyr Leu
    50                  55                  60

Met Ala Asn Glu Arg Met Asn Leu Met Asn Met Ala Lys Leu Ser Ile
65                  70                  75                  80

Lys Gly Leu Ile Glu Ser Ala Leu Asn Leu Gly Arg Thr Leu Asp Ser
                85                  90                  95

Asp Tyr Ala Pro Leu Gln Gln Phe Phe Val Val Met Glu His Cys Leu
            100                 105                 110

Lys His Gly Leu Lys Ala Lys Lys Thr Phe Leu Gly Gln Asn Lys Ser
        115                 120                 125

Phe Trp Gly Pro Leu Glu Leu Val Glu Lys Leu Val Pro Glu Ala Ala
    130                 135                 140

Glu Ile Thr Ala Ser Val Lys Asp Leu Pro Gly Leu Lys Thr Pro Val
145                 150                 155                 160

Gly Arg Gly Arg Ala Trp Leu Arg Leu Ala Leu Met Gln Lys Lys Leu
                165                 170                 175

Ser Glu Tyr Met Lys Ala Leu Ile Asn Lys Lys Glu Leu Leu Ser Glu
            180                 185                 190

Phe Tyr Glu Ala Asn Ala Leu Met Met Glu Glu Gly Ala Ile Ile
        195                 200                 205

Ala Gly Leu Leu Val Gly Leu Asn Val Ile Asp Ala Asn Phe Cys Met
    210                 215                 220

Lys Gly Glu Asp Leu Asp Ser Gln Val Gly Val Ile Asp Phe Ser Met
```

```
                225                 230                 235                 240
Tyr Leu Lys Asp Gly Asn Ser Lys Gly Ser Glu Gly Asp Gly Gln
                245                 250                 255
Ile Thr Ala Ile Leu Asp Gln Lys Asn Tyr Val Glu Glu Leu Asn Arg
                260                 265                 270
His Leu Asn Ala Thr Val Asn Asn Leu Gln Ala Lys Val Asp Ala Leu
                275                 280                 285
Glu Lys Ser Asn Thr Lys Leu Thr Glu Glu Leu Ala Val Ala Asn Asn
                290                 295                 300
Arg Ile Ile Thr Leu Gln Glu Glu Met Glu Arg Val Lys Glu Glu Ser
305                 310                 315                 320
Ser Tyr Leu Leu Glu Ser Asn Arg Lys Gly Pro Lys Gln Asp Arg Thr
                325                 330                 335
Ala Glu Gly Gln Ala Leu Ser Glu Ala Arg Lys His Leu Lys Glu Glu
                340                 345                 350
Thr Gln Leu Arg Leu Asp Val Glu Lys Glu Leu Glu Leu Gln Ile Ser
                355                 360                 365
Met Arg Gln Glu Met Glu Leu Ala Met Lys Met Leu Glu Lys Asp Val
    370                 375                 380
Cys Glu Lys Gln Asp Ala Leu Val Ser Leu Arg Gln Gln Leu Asp Asp
385                 390                 395                 400
Leu Arg Ala Leu Lys His Glu Leu Ala Phe Lys Leu Gln Ser Ser Asp
                405                 410                 415
Leu Gly Val Lys Gln Lys Ser Glu Leu Asn Ser Arg Leu Glu Glu Lys
                420                 425                 430
Thr Asn Gln Met Ala Ala Thr Ile Lys Gln Leu Glu Gln Ser Glu Lys
                435                 440                 445
Asp Leu Val Lys Gln Ala Lys Thr Leu Asn Ser Ala Ala Asn Lys Leu
                450                 455                 460
Ile Pro Lys His His
465

<210> SEQ ID NO 9
<211> LENGTH: 1464
<212> TYPE: DNA
<213> ORGANISM: Rattus norvegicus
<220> FEATURE:
<221> NAME/KEY: CDS
<222> LOCATION: (1)..(1464)

<400> SEQUENCE: 9 atg tct gcc ctg acg cct ccg act gat atg cca acc ccc acc act gac    48
Met Ser Ala Leu Thr Pro Pro Thr Asp Met Pro Thr Pro Thr Thr Asp
1               5                   10                  15 aag ata acc cag gct gcc atg gag acc atc tac ctc tgc aaa ttc cgg    96
Lys Ile Thr Gln Ala Ala Met Glu Thr Ile Tyr Leu Cys Lys Phe Arg
                20                  25                  30 gtg tct atg gat gga gaa tgg ctc tgc ctt cga gag ctg gat gac atc   144
Val Ser Met Asp Gly Glu Trp Leu Cys Leu Arg Glu Leu Asp Asp Ile
            35                  40                  45 tcc ctt aca cct gac cca gag cct acc cat gaa gac tct tgg gag gat   192
Ser Leu Thr Pro Asp Pro Glu Pro Thr His Glu Asp Ser Trp Glu Asp
        50                  55                  60 ttg aca gat ttg gtg gag caa gtg cgt gct gac cca gaa gat cct aat   240
Leu Thr Asp Leu Val Glu Gln Val Arg Ala Asp Pro Glu Asp Pro Asn
65                  70                  75                  80 tat ctc atg gct aac gag cgc atg aac ctg atg aac atg gcg aag ctg   288
Tyr Leu Met Ala Asn Glu Arg Met Asn Leu Met Asn Met Ala Lys Leu
```

|  |  |  |  |  |  |  |  |  |  |  |  |  |
|---|---|---|---|---|---|---|---|---|---|---|---|---|
|  |  | 85 |  |  |  | 90 |  |  |  | 95 |  |  |

```
agc atc aag ggc ttg att gag tcg gct ctg aac ctg ggg cgg acc ctg       336
Ser Ile Lys Gly Leu Ile Glu Ser Ala Leu Asn Leu Gly Arg Thr Leu
            100                 105                 110 gac tct gac tac gca cct ctc cag cag ttc ttc gtg gtg atg gaa cac       384
Asp Ser Asp Tyr Ala Pro Leu Gln Gln Phe Phe Val Val Met Glu His
        115                 120                 125 tgc ctg aaa cat ggc ttg aaa gcc aag aaa act ttt ctt gga caa aat       432
Cys Leu Lys His Gly Leu Lys Ala Lys Lys Thr Phe Leu Gly Gln Asn
130                 135                 140 aag tcc ttc tgg ggt cct cta gag ctg gta gaa aag ctt gtt cca gaa       480
Lys Ser Phe Trp Gly Pro Leu Glu Leu Val Glu Lys Leu Val Pro Glu
145                 150                 155                 160 gct gca gag ata aca gca agt gta aaa gat ctc cca gga ctc aag aca       528
Ala Ala Glu Ile Thr Ala Ser Val Lys Asp Leu Pro Gly Leu Lys Thr
                165                 170                 175 cca gtt ggc aga gga aga gcc tgg ctt cgg ttg gca tta atg caa aag       576
Pro Val Gly Arg Gly Arg Ala Trp Leu Arg Leu Ala Leu Met Gln Lys
            180                 185                 190 aag ctt tct gag tac atg aag gcc ttg atc aat aag aag gaa ctt ctc       624
Lys Leu Ser Glu Tyr Met Lys Ala Leu Ile Asn Lys Lys Glu Leu Leu
        195                 200                 205 agt gag ttc tat gaa gcc aat gct ctc atg atg gaa gaa gaa ggc gca       672
Ser Glu Phe Tyr Glu Ala Asn Ala Leu Met Met Glu Glu Glu Gly Ala
210                 215                 220 att att gct ggc ctc ctg gtc ggt ctg aat gtc atc gat gcc aat ttc       720
Ile Ile Ala Gly Leu Leu Val Gly Leu Asn Val Ile Asp Ala Asn Phe
225                 230                 235                 240 tgc atg aaa gga gaa gac ctg gac tct cag gtt ggc gtt ata gac ttt       768
Cys Met Lys Gly Glu Asp Leu Asp Ser Gln Val Gly Val Ile Asp Phe
                245                 250                 255 tca atg tat ctc aaa gat ggg aac agc agt aaa ggc agt gaa ggg gat       816
Ser Met Tyr Leu Lys Asp Gly Asn Ser Ser Lys Gly Ser Glu Gly Asp
            260                 265                 270 gga cag att act gcg att ctg gac cag aaa aac tat gta gaa gaa ctc       864
Gly Gln Ile Thr Ala Ile Leu Asp Gln Lys Asn Tyr Val Glu Glu Leu
        275                 280                 285 aac aga cat ctg aat gct act gta aac aac ctt cag gca aaa gta gat       912
Asn Arg His Leu Asn Ala Thr Val Asn Asn Leu Gln Ala Lys Val Asp
290                 295                 300 gcg tta gaa aaa tcc aac acg aaa ttg aca gag gaa ctt gcc gtc gcc       960
Ala Leu Glu Lys Ser Asn Thr Lys Leu Thr Glu Glu Leu Ala Val Ala
305                 310                 315                 320 aac aac aga att att acc tta caa gaa gaa atg gaa cgg gtt aaa gaa      1008
Asn Asn Arg Ile Ile Thr Leu Gln Glu Glu Met Glu Arg Val Lys Glu
                325                 330                 335 gaa agt tcc tat cta ctg gaa tcc aat cgg aag ggt cct aag caa gac      1056
Glu Ser Ser Tyr Leu Leu Glu Ser Asn Arg Lys Gly Pro Lys Gln Asp
            340                 345                 350 aga act gca gaa ggg caa gcg ctg agc gaa gcc aga aag cat cta aag      1104
Arg Thr Ala Glu Gly Gln Ala Leu Ser Glu Ala Arg Lys His Leu Lys
        355                 360                 365 gag gag aca cag tta cga ttg gac gtt gaa aag gag ctg gag ctg cag      1152
Glu Glu Thr Gln Leu Arg Leu Asp Val Glu Lys Glu Leu Glu Leu Gln
370                 375                 380 atc agc atg agg cag gag atg gaa ctg gct atg aag atg ctg gag aag      1200
Ile Ser Met Arg Gln Glu Met Glu Leu Ala Met Lys Met Leu Glu Lys
385                 390                 395                 400 gat gtc tgt gag aag cag gat gcc ctg gtg tcc ctg cgg cag cag ctg      1248
Asp Val Cys Glu Lys Gln Asp Ala Leu Val Ser Leu Arg Gln Gln Leu
```

-continued

```
                    405                 410                 415
gat gat ctc cga gct ctt aaa cac gag ctt gcc ttt aag ctg cag agt         1296
Asp Asp Leu Arg Ala Leu Lys His Glu Leu Ala Phe Lys Leu Gln Ser
            420                 425                 430 tca gac cta gga gtg aaa cag aaa agt gaa tta aac agt cgc ttg gaa         1344
Ser Asp Leu Gly Val Lys Gln Lys Ser Glu Leu Asn Ser Arg Leu Glu
        435                 440                 445 gag aag acc aat cag atg gct gcc acc att aaa cag ctg gag caa agt         1392
Glu Lys Thr Asn Gln Met Ala Ala Thr Ile Lys Gln Leu Glu Gln Ser
    450                 455                 460 gaa aaa gat ttg gtg aaa cag gca aag acc tta aat agt gca gca aat         1440
Glu Lys Asp Leu Val Lys Gln Ala Lys Thr Leu Asn Ser Ala Ala Asn
465                 470                 475                 480 aaa ctg atc cca aaa cat cat tag                                         1464
Lys Leu Ile Pro Lys His His
                485

<210> SEQ ID NO 10
<211> LENGTH: 487
<212> TYPE: PRT
<213> ORGANISM: Rattus norvegicus

<400> SEQUENCE: 10

Met Ser Ala Leu Thr Pro Pro Thr Asp Met Pro Thr Pro Thr Thr Asp
1               5                   10                  15

Lys Ile Thr Gln Ala Ala Met Glu Thr Ile Tyr Leu Cys Lys Phe Arg
            20                  25                  30

Val Ser Met Asp Gly Glu Trp Leu Cys Leu Arg Glu Leu Asp Asp Ile
        35                  40                  45

Ser Leu Thr Pro Asp Pro Glu Pro Thr His Glu Asp Ser Trp Glu Asp
    50                  55                  60

Leu Thr Asp Leu Val Glu Gln Val Arg Ala Asp Pro Glu Asp Pro Asn
65                  70                  75                  80

Tyr Leu Met Ala Asn Glu Arg Met Asn Leu Met Asn Met Ala Lys Leu
                85                  90                  95

Ser Ile Lys Gly Leu Ile Glu Ser Ala Leu Asn Leu Gly Arg Thr Leu
            100                 105                 110

Asp Ser Asp Tyr Ala Pro Leu Gln Gln Phe Phe Val Val Met Glu His
        115                 120                 125

Cys Leu Lys His Gly Leu Lys Ala Lys Lys Thr Phe Leu Gly Gln Asn
    130                 135                 140

Lys Ser Phe Trp Gly Pro Leu Glu Leu Val Lys Leu Val Pro Glu
145                 150                 155                 160

Ala Ala Glu Ile Thr Ala Ser Val Lys Asp Leu Pro Gly Leu Lys Thr
                165                 170                 175

Pro Val Gly Arg Gly Arg Ala Trp Leu Arg Leu Ala Leu Met Gln Lys
            180                 185                 190

Lys Leu Ser Glu Tyr Met Lys Ala Leu Ile Asn Lys Lys Glu Leu Leu
        195                 200                 205

Ser Glu Phe Tyr Glu Ala Asn Ala Leu Met Met Glu Glu Glu Gly Ala
    210                 215                 220

Ile Ile Ala Gly Leu Leu Val Gly Leu Asn Val Ile Asp Ala Asn Phe
225                 230                 235                 240

Cys Met Lys Gly Glu Asp Leu Asp Ser Gln Val Gly Val Ile Asp Phe
                245                 250                 255

Ser Met Tyr Leu Lys Asp Gly Asn Ser Ser Lys Gly Ser Glu Gly Asp
            260                 265                 270
```

Gly Gln Ile Thr Ala Ile Leu Asp Gln Lys Asn Tyr Val Glu Glu Leu
            275                 280                 285

Asn Arg His Leu Asn Ala Thr Val Asn Asn Leu Gln Ala Lys Val Asp
    290                 295                 300

Ala Leu Glu Lys Ser Asn Thr Lys Leu Thr Glu Leu Ala Val Ala
305                 310                 315                 320

Asn Asn Arg Ile Ile Thr Leu Gln Glu Glu Met Glu Arg Val Lys Glu
                325                 330                 335

Glu Ser Ser Tyr Leu Leu Glu Ser Asn Arg Lys Gly Pro Lys Gln Asp
            340                 345                 350

Arg Thr Ala Glu Gly Gln Ala Leu Ser Glu Ala Arg Lys His Leu Lys
    355                 360                 365

Glu Glu Thr Gln Leu Arg Leu Asp Val Glu Lys Glu Leu Glu Leu Gln
    370                 375                 380

Ile Ser Met Arg Gln Glu Met Glu Leu Ala Met Lys Met Leu Glu Lys
385                 390                 395                 400

Asp Val Cys Glu Lys Gln Asp Ala Leu Val Ser Leu Arg Gln Gln Leu
                405                 410                 415

Asp Asp Leu Arg Ala Leu Lys His Glu Leu Ala Phe Lys Leu Gln Ser
            420                 425                 430

Ser Asp Leu Gly Val Lys Gln Lys Ser Glu Leu Asn Ser Arg Leu Glu
            435                 440                 445

Glu Lys Thr Asn Gln Met Ala Ala Thr Ile Lys Gln Leu Glu Gln Ser
    450                 455                 460

Glu Lys Asp Leu Val Lys Gln Ala Lys Thr Leu Asn Ser Ala Ala Asn
465                 470                 475                 480

Lys Leu Ile Pro Lys His His
                485

<210> SEQ ID NO 11
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
cucuagagcu gguagaaaa                                                19

<210> SEQ ID NO 12
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
ggcaaaagua gaugcguua                                                19

<210> SEQ ID NO 13
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13

```
agcgaagguu gacgcucuu                                                    19

<210> SEQ ID NO 14
<211> LENGTH: 18
<212> TYPE: PRT
<213> ORGANISM: Unknown
<220> FEATURE:
<223> OTHER INFORMATION: Description of Unknown Organism: Singar2
      peptide

<400> SEQUENCE: 14

Glu Asp Ser Trp Glu Asp Leu Thr Asp Leu Val Glu Gln Val Arg Ala
1               5                   10                  15

Asp Pro
```